(12) United States Patent
Wolf et al.

(10) Patent No.: US 9,815,746 B2
(45) Date of Patent: Nov. 14, 2017

(54) STEREODYNAMIC CHEMOSENSORS

(71) Applicant: GEORGETOWN UNIVERSITY, Washington, DC (US)

(72) Inventors: Christian Wolf, Arlington, VA (US); Keith W. Bentley, Washington, DC (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/776,538

(22) PCT Filed: Mar. 14, 2014

(86) PCT No.: PCT/US2014/028500
§ 371 (c)(1),
(2) Date: Sep. 14, 2015

(87) PCT Pub. No.: WO2014/144197
PCT Pub. Date: Sep. 18, 2014

(65) Prior Publication Data
US 2016/0039723 A1 Feb. 11, 2016

Related U.S. Application Data

(60) Provisional application No. 61/800,499, filed on Mar. 15, 2013, provisional application No. 61/813,840, filed on Apr. 19, 2013.

(51) Int. Cl.
| | | |
|---|---|---|
| *C07C 47/57* | (2006.01) | |
| *C07D 217/16* | (2006.01) | |
| *C07D 213/89* | (2006.01) | |
| *C07B 57/00* | (2006.01) | |

(52) U.S. Cl.
CPC ............. *C07B 57/00* (2013.01); *C07C 47/57* (2013.01); *C07D 213/89* (2013.01); *C07D 217/16* (2013.01)

(58) Field of Classification Search
CPC .... C07B 57/00; C07D 213/89; C07D 217/16; C07C 47/57
See application file for complete search history.

(56) References Cited

U.S. PATENT DOCUMENTS

| | | |
|---|---|---|
| 7,888,509 B2 | 2/2011 | Wolf et al. |
| 8,034,621 B2 | 10/2011 | Rao et al. |
| 2004/0173777 A1 | 9/2004 | Morton et al. |
| 2007/0125712 A1 | 6/2007 | Little et al. |
| 2007/0276140 A1 | 11/2007 | Wolf et al. |
| 2010/0227766 A1 | 9/2010 | Walt et al. |
| 2012/0129204 A1 | 5/2012 | Fabrega et al. |

FOREIGN PATENT DOCUMENTS

WO   WO 2012/138654   10/2012

OTHER PUBLICATIONS

Lima, C.F., "Elucidating the Role of Aromatic Interactions in Rotational Barriers Involving Aromatic Systems." The Journal of organic chemistry 77.22 (2012): 10422-10426.*
Suvitha, A., "NBO, HOMO-LUMO, UV, NLO, NMR and vibrational analysis of veratrole using FT-IR, FT-Raman, FT-NMR spectra and HF-DFT computational methods." Spectrochimica Acta Part A: Molecular and Biomolecular Spectroscopy 138 (2015): 357-369.*
Ghosn, M.W.,"Synthesis, conformational stability, and asymmetric transformation of atropisomeric 1, 8-bisphenolnaphthalenes." The Journal of organic chemistry 76.10 (2011): 3888-3897.*
Altun, A., "Structural and spectroscopic (UV-VIS, IR, Raman, and NMR) characteristics of anisaldehydes that are flavoring food additives: A density functional study in comparison with experiments." Journal of Molecular Structure 1128 (2017): 590-605.*
Matyasovszky, N., "Kinetic study of the electrochemical oxidation of salicylic acid and salicylaldehyde using UV/vis spectroscopy and multivariate calibration." The Journal of Physical Chemistry A 113.33 (2009): 9348-9353.*
UV and Visible Absorption Techniques vol. 1 Chap 2 "UV, Principles of. A. The Origin of Absorption."; downloaded Dec. 19, 2016: http://matematicas.udea.edu.co/~carlopez/uv_vis_pharmacy_full.pdf p. 31-125.*
Liu, S. et al., "Enantioselective Fluorescence Sensing of Chiral Alpha-Amino Alcohols", J. Org. Chem., vol. 73, Mar. 2008, p. 4267-4270; p. 4267, paragraph [0001].
International Search Report issued in corresponding PCT International Application No. PCT/US2014/028500 and the Written Opinion.
PCT/US2014/028500, International Preliminary Report on Patentability (Sep. 15, 2015).

* cited by examiner

*Primary Examiner* — Matt Mauro
(74) *Attorney, Agent, or Firm* — LeClairRyan, a Professional Corporation

(57) ABSTRACT

The present invention relates to multifunctional chemosensors that can measure the concentration, enantiomeric excess (ee), and absolute configuration of chiral compounds. The chemosensors described herein may contain a backbone moiety that is bonded to a fluorescent moiety and a moiety for bonding a chiral compound. Backbone moieties may include aromatic groups, for example, naphthyl. The chemosensors described herein are useful for measuring concentration, enantiomeric excess, and absolute configuration of organic molecules in areas such as high throughput screening.

20 Claims, 25 Drawing Sheets

STEREODYNAMIC CHEMOSENSORS

INCORPORATION BY REFERENCE

This application claims the benefit of priority of U.S. Provisional Application No. 61/800,499, filed Mar. 15, 2013 and U.S. Provisional Application No. 61/813,840, filed Apr. 19, 2013.

The documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

STATEMENT OF GOVERNMENT INTEREST

This invention was made in part with government support under grant number CHE 1213019 awarded by the U.S. National Science Foundation (NSF). The government has certain rights to this invention.

BACKGROUND

The ever-increasing demand for new biologically active chiral compounds, in particular pharmaceuticals and agrochemicals, continues to nurture tremendous interest in asymmetric synthesis.[1] The development of enantioselective reactions for the production of chiral compounds is vigorously pursued at numerous academic and industrial research laboratories, and the pace and prospect of these efforts have increased significantly during the last 20 years with the introduction of combinatorial methods. In contrast, the analysis of the amount and enantiomeric composition of chiral compounds has become a major bottleneck in the discovery process.

High-throughput screening (HTS) methods capable of analyzing large numbers of samples that can be generated overnight are required to match the productivity of parallel synthesis and other combinatorial techniques. It has been proposed that optical methods based on fluorescence, UV and circular dichroism spectroscopy hold considerable promise toward the goal of enantioselective HTS.[2] Several optical sensing assays developed to date have been found to outperform chromatographic and NMR spectroscopic methods with regard to time-efficiency, sensitivity and waste production.[3-5]

Optical assays typically provide information on the enantiomeric excess but require independent analysis of the concentration of the substrate tested unless two chemosensors are used simultaneously or in tandem.[6] Because a complete stereochemical analysis must reveal the absolute configuration, the enantiomeric composition, and the total concentration of a chiral compound, the development of a widely useful and practical probe that can accomplish all three tasks with high accuracy is a significant challenge in the field of organic chemistry. To become practical for HTS purposes, the processes described above have to occur within a few minutes and generate strong (chir)optical responses that can be accurately quantified.

SUMMARY OF THE INVENTION

The present invention relates to multifunctional chemosensors that can measure the concentration, enantiomeric excess, and/or absolute configuration of chiral compounds. In certain aspects of the invention, a single probe can measure two or more of the parameters of concentration, enantiomeric excess, and absolute configuration. In certain aspects, a single probe can measure all three parameters of concentration, enantiomeric excess, and absolute configuration.

The chemosensors of the present invention comprise a fluorescent and/or UV active moiety and a moiety for bonding a chiral compound. In an embodiment, the chemosensors of the invention undergo rapid racemization and/or diastereomerization at room temperature. In an embodiment, the chemosensors of the invention are themselves achiral. In an embodiment, the chemosensors of the invention are themselves chiral.

In a specific embodiment, the chemosensor comprises a backbone moiety that is bonded to a fluorescent moiety and a moiety for bonding a chiral compound. In an embodiment, the backbone moiety is an aromatic group. In another embodiment, the backbone moiety is a naphthyl group that may optionally be substituted with additional chemical groups.

In an embodiment of the present invention, the chemosensor is a compound of formula (I):

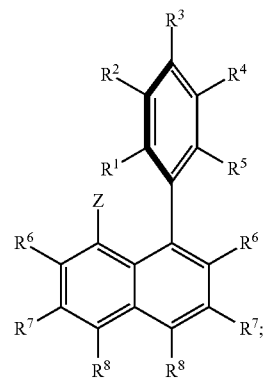

wherein
$R^1$ and $R^5$ are independently hydrogen, halo, cyano, ($C_1$-$C_3$) alkyl, ($C_2$-$C_3$) alkenyl, or ($C_2$-$C_3$) alkynyl;
$R^2$ and $R^4$ are independently hydrogen, —$CO_2R^9$, —$C(O)N(R^9)_2$, —$NR^9$—(C=$NR^9$)$N(R^9)_2$, —$NR^9$—(C=O)$OR^9$, —O—(C=O)$N(R^9)_2$, —$C(O)R^9$, $C(O)CF_3$, —(C=NH)$R^9$, $N(R^9)_2$, $OR^9$, or $SR^9$ wherein at least one $R^2$ and $R^4$ is not hydrogen;
$R^3$ is —$CO_2R^9$, —$C(O)N(R^9)_2$, —$NR^9$—(C=$NR^9$)$N(R^9)_2$, —$NR^9$—(C=O)$OR^9$, —O—(C=O)$N(R^9)_2$, —$C(O)$ $R^9$, $C(O)CF_3$, —(C=NH)$R^9$, $N(R^9)_2$, $OR^9$, or $SR^9$,
each $R^6$ is independently hydrogen, halo, cyano, ($C_1$-$C_3$) alkyl, ($C_2$-$C_3$) alkenyl, or ($C_2$-$C_3$) alkynyl;
$R^7$ and $R^8$ are independently hydrogen, ($C_1$-$C_6$) alkyl, ($C_2$-$C_6$) alkenyl; ($C_2$-$C_6$) alkynyl, aryl, heteroaryl, cyano, nitro, halo, or trihalomethyl;
each $R^9$ is independently hydrogen, ($C_1$-$C_6$) alkyl, or aryl; and
Z is a fluorescent moiety, a UV active moiety, or a moiety with fluorescent and UV active properties.

In an embodiment of formula (I), Z is an aryl or heteroaryl group, wherein the aryl or heteroaryl group may be substituted or unsubstituted.

In another embodiment of the present invention, the chemosensor of formula (I) is a compound of formula (II):

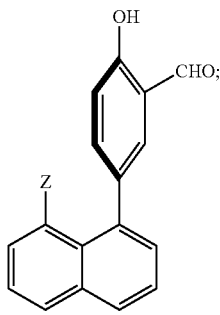

II wherein Z is a fluorescent moiety, a UV active moiety, or a moiety with fluorescent and UV active properties.

In an embodiment of formula (II), Z is an aryl or heteroaryl group, wherein the aryl or heteroaryl group may be substituted or unsubstituted.

In an embodiment of formula (I) or formula (II), Z is an anthracene, an isoquinoline-N-oxide, a quinoline-N-oxide, or a pyridyl-N-oxide.

In an embodiment of the present invention, the chemosensor of formula (I) is a compound of formula 1:

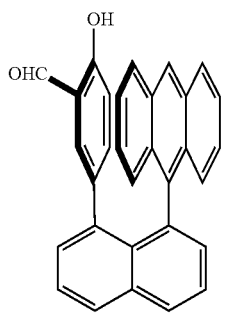

1

In an embodiment of the present invention, the chemosensor of formula (I) is a compound of formula 2:

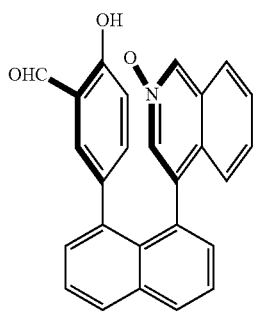

2

In an embodiment of the present invention, the chemosensor of formula (I) is a compound of formula 3:

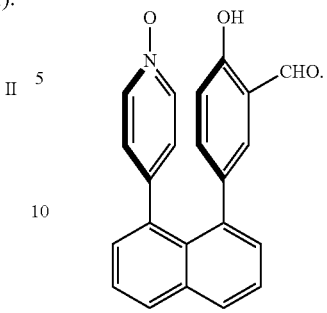

3

The present invention also relates to methods of determining one or more analytical parameters on a chiral substrate compound, wherein the analytical parameters are selected from enantiomeric excess determination (ee), absolute stereochemistry determination, and concentration. Methods of the invention comprise combining a compound of formula (I) with a chiral substrate compound, and then determining the ee, absolute stereochemistry, and/or the concentration by means known to those of skill in the art.

In a specific embodiment, a determination of two or more of: absolute configuration of the major enantiomer, the ee, and/or the total substrate concentration of a compound can all be accomplished on a single solution by combining a compound of formula (I) with a substrate compound, and then making the appropriate analytical determination by means known to those of skill in the art.

In a specific embodiment, a determination of the absolute configuration of the major enantiomer, the ee, and the total substrate concentration of a compound can all be accomplished on a single solution by combining a compound of formula (I) with a substrate compound, and then making the appropriate analytical determination by means known to those of skill in the art.

These aspects of the invention and other aspects of the invention are disclosed or are apparent from and encompassed by, the Detailed Description which follows below.

For the purposes of this application the following terms may have the meanings defined below:

"atropisomer"—stereoisomers resulting from hindered rotation about single bonds where the steric strain barrier to rotation might be high enough to allow for the isolation of conformers.

"de"—diastereomeric excess.

"ee"—enantiomeric excess.

"hydroxy protecting group"—refers to known —OH protecting groups to those of skill in the art which includes, but is not limited to those described in *Protective Groups in Organic Synthesis (Fourth Edition)*, Theodora W. Greene and Peter G. M. Wuts, Wiley-Interscience (October 2006).

For the compound of formula (I) and all subsequent formulae, terms for chemical radicals are used are defined as follows. Groups that described as "substituted" may be substituted with one or more of the following groups described below.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indanyl, etc.; this applies correspondingly to hydrocarbon radicals in composite meanings, such as hydrocarbonoxy radicals or other hydrocarbon radicals attached via heteroatom groups.

The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton. In certain embodiment, the hydrocarbon radicals of the present invention may either be substituted or unsubstituted.

By way of example, the expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, for example "$(C_1-C_6)$-alkyl" correspondingly also include straight-chain or branched alkyl radicals having a larger number of carbon atoms, i.e., according to the example, also the alkyl radicals having 5 and 6 carbon atoms.

Alkyl radicals, including in the combined definitions such as alkoxy, haloalkyl, etc., are, for example, methyl, ethyl, n- or i-propyl, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, also allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl. Alkynyl also includes, in particular, straight-chain or branched hydrocarbon radicals having more than one triple bond or else having one or more triple bonds and one or more double bonds, for example 1,3-butatrienyl or 3-penten-1-yn-1-yl(pent-3-en-1-yn-1-yl).

A carbocyclic ring is any form of a closed ring of carbon atoms and can include alicyclic or aromatic structures. Examples of such structures include, but are not limited to $(C_3-C_9)$-cycloalkyl which is a carbocyclic saturated ring system having 3-9 ring carbon atoms, for example cyclopropyl, cyclobutyl, cyclopentyl, cyclohexyl, cydoheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene. Further examples include, but are not limited to $(C_5-C_9)$-cycloalkenyl which is a carbocyclic, nonaromatic, partially unsaturated ring system having 5-9 ring carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$-alkylidene, is the radical of a straight-chain or branched alkane which is bonded via a double bond, the position of the binding site not being fixed. In the case of a branched alkane, of course, only positions at which two hydrogen atoms may be replaced by the double bond are possible; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are, respectively, alkyl, alkenyl and alkynyl substituted partly or fully by identical or different halogen atoms, preferably from the group of fluorine, chlorine and bromine, in particular from the group of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl and other halogen-substituted radicals.

Aryl is a mono-, bi- or polycyclic carbocyclic aromatic system, for example phenyl, naphthyl, tetrahydronaphthyl, indenyl, indanyl, pentalenyl, fluorenyl and the like.

Optionally substituted aryl also includes polycyclic systems, such as tetrahydronaphthyl, indenyl, indanyl, fluorenyl, biphenylyl, where the point of attachment is at the aromatic system.

A heterocyclic radical (heterocyclyl) comprises at least one heterocyclic ring (=carbocyclic ring in which at least one carbon atom is replaced by a heteroatom, e.g. by a heteroatom from the group consisting of N, O, S, P, B, Si, Se), which is saturated, unsaturated or heteroaromatic and may be unsubstituted or substituted, where the point of attachment is located at a ring atom.

If the heterocyclyl radical or the heterocyclic ring is optionally substituted, it can be fused to other carbocyclic or heterocyclic rings.

Optionally substituted heterocyclyl also includes polycyclic systems, such as, for example, 8-aza-bicyclo[3.2.1]octanyl or 1-aza-bicyclo[2.2.1]heptyl.

Optionally substituted heterocyclyl also includes spirocyclic systems, such as, for example, 1-oxa-5-aza-spiro[2.3]hexyl.

Heteroaryl means, from among the systems defined above under "heterocyclyl", in each case a heteroaromatic compound, i.e. a fully unsaturated aromatic heterocyclic compound.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, 1, 2 or 3, radicals selected from the group of halogen, alkoxy, alkylthio, $SF_5$, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, alkylsulfonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as the substituted alkyl, alkenyl, alkynyl, cycloalkyl, aryl, phenyl, benzyl, heterocyclyl and heteroaryl radicals mentioned, substituents include, in addition to the saturated hydrocarbon radicals mentioned such as alkyl, alkoxy, alkylthio, alkoxycarbonyl, haloalkyl, cycloalkyl or cycloalkyloxy, corresponding unsaturated aliphatic and aromatic radicals, such as optionally substituted alkenyl, alkynyl, alkenyloxy, alkynyloxy, phenyl and phenoxy. In the case of substituted cyclic radicals having aliphatic moieties in the ring, cyclic systems with those substituents which are bonded on the ring by a double bond are also included, for example substituted by an alkylidene group such as methylidene or ethylidene.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulfonic acids, sulfinic acids, N-substituted sulfonamide acids, phosphonic acids or phosphinic acids.

In certain embodiments described herein, "rapid" or "fast" racemization and/or diastereomerization may refer to racemization and/or diastereomerization that takes place in less than about an hour, less than about 45 minutes, less than about 30 minutes, less than about 20 minutes, less than about 15 minutes, less than about 10 minutes, less than about 5 minutes, less than about 3 minutes, less than about 2 minutes, less than about 1 minute, or less than about 30 seconds.

The "yl position" of a radical denotes the carbon atom having the free bond.

As described herein, fluorescent moieties or fluorophores is a chemical group, which when excited by exposure to a particular stimulus, such as a defined wavelength of light, emits light (fluoresces), for example at a different wavelength (such as a longer wavelength of light). For the purpose of this application, these terms may be used interchangeably.

Specific "fluorescent moieties" or "fluorophores" that are known to those of skill in the art and include those provided in U.S. Pat. No. 5,866,366 to Nazarenko et al., such as 4-acetamido-4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcoluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), 6-carboxy-fluorescein (HEX), and TET (tetramethyl fluorescein); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate, and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; Cy3; Cy5, VIC® (Applied Biosystems); LC Red 640; LC Red 705; and Yakima yellow amongst others. Additional examples of fluorophores include Quasar® 670, Quasar® 570, CAL Fluor® Red 590, CAL Fluor® Red 610, CAL Fluor® 615, CAL Fluor® Red 635, CAL Fluor® Green 520, CAL Fluor® Gold 540, and CAL Fluor® Orange 560 (Biosearch Technologies, Novato, Calif.).

In an embodiment, the fluorescent moiety is an aryl or heteroaryl moiety.

In an embodiment, the fluorescent moiety is an anthracene, a quinoline N-oxide, an isoquinoline N-oxide, or a pyridyl N-oxide.

In an embodiment, the fluorescent moiety is 4'-pyridyl-N-oxide.

The fluorophores described above may be modified so that they can be bonded in the Z position of formula (I). Such chemical modifications may be known to those of ordinary skill in the art, or synthetic techniques described herein may be used to achieve the chemical conversion.

Other suitable fluorophores include those known to those skilled in the art, for example those available from Molecular Probes/Life Technologies (Carlsbad, Calif.). In particular examples, a fluorophore is used as a donor fluorophore or as an acceptor fluorophore In addition, for the purposes of this application compounds of the invention also include all stereoisomers and racemic mixtures thereof. The possible stereoisomers defined by their specific three-dimensional shape, such as enantiomers, diastereomers, Z- and E-isomers, and atropisomers are all encompassed by the formula (I) and can, in the enantioselective procedure, be prepared selectively when optically active materials are used. The application also includes all tautomeric forms, pharmaceutically acceptable salts, and crystalline forms including polymorphic forms.

It is further noted that the invention does not intend to encompass within the scope of the invention any previously disclosed product or composition, process of making the product or composition, or method of using the product or composition, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

These and other embodiments are disclosed or are apparent from and encompassed by the following Detailed Description.

DETAILED DESCRIPTION OF THE INVENTION

Figure 1:
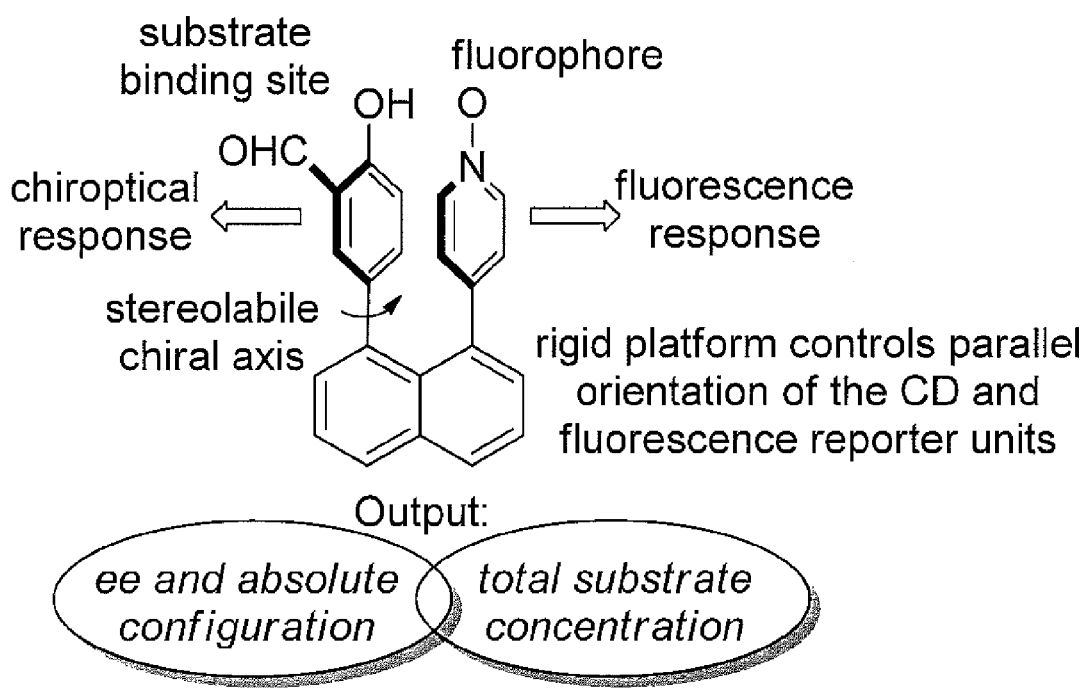
FIG. 1: Design of a sensor with CD and fluorescence reporter units.

Because a complete stereochemical analysis must reveal the absolute configuration, the enantiomeric composition, and the total concentration of a chiral compound, the present invention relates to a widely useful, practical probe that can accomplish all three tasks with high accuracy and sensitivity. This has been shown to be possible with multifunctional chemical chemosensors.

In an embodiment of the present invention, the chemosensor is a compound of formula (I):

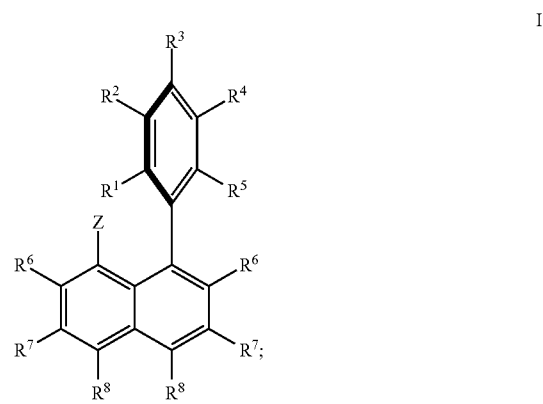

wherein $R^1$ and $R^5$ are independently hydrogen, halo, cyano, (C$_1$-C$_3$) alkyl, (C$_2$-C$_3$) alkenyl, or (C$_2$-C$_3$) alkynyl;

$R^2$ and $R^4$ are independently hydrogen, —CO$_2$R$^9$, —C(O)N(R$^9$)$_2$, —NR$^9$—(C═NR$^9$)N(R$^9$)$_2$, —NR$^9$—(C═O)OR$^9$, —O—(C═O)N(R$^9$)$_2$, —C(O)R$^9$, C(O)CF$_3$, —(C═NH)R$^9$, N(R$^9$)$_2$, OR$^9$, or SR$^9$ wherein at least one $R^2$ and $R^4$ is not hydrogen;

$R^3$ is —CO$_2$R$^9$, —C(O)N(R$^9$)$_2$, —NR$^9$—(C═NR$^9$)N(R$^9$)$_2$, —NR$^9$—(C═O)OR$^9$, —O—(C═O)N(R$^9$)$_2$, —C(O)R$^9$, C(O)CF$_3$, —(C═NH)R$^9$, N(R$^9$)$_2$, OR$^9$, or SR$^9$, each $R^6$ is independently hydrogen, halo, cyano, (C$_1$-C$_3$) alkyl, (C$_2$-C$_3$) alkenyl, or (C$_2$-C$_3$) alkynyl;

$R^7$ and $R^8$ are independently hydrogen, (C$_1$-C$_6$) alkyl, (C$_2$-C$_6$) alkenyl; (C$_2$-C$_6$) alkynyl, aryl, heteroaryl, cyano, nitro, halo, or trihalomethyl;

each $R^9$ is independently hydrogen, (C$_1$-C$_6$) alkyl, or aryl; and

Z is a fluorescent moiety, a UV active moiety, or a moiety with fluorescent and UV active properties.

In an embodiment of formula (I), $R^1$ and $R^5$ are independently hydrogen or methyl.

In another embodiment of formula (I), $R^1$ and $R^5$ are hydrogen.

In an embodiment of formula (I), $R^2$ and $R^4$ are each independently hydrogen, —CHO, or —(CO)(C$_1$-C$_6$) alkyl, wherein at least one $R^2$ and $R^4$ is not hydrogen.

In another embodiment of formula (I), $R^2$ and $R^4$ are each independently hydrogen or —CHO, wherein at least one $R^2$ and $R^4$ is not hydrogen.

In an embodiment of formula (I), $R^3$ is NHR$^9$, SR$^9$, or OH, wherein R$^9$ is hydrogen or a (C$_1$-C$_6$)alkyl.

In another embodiment of formula (I), $R^3$ is OH.

In an embodiment of formula (I), $R^6$ is hydrogen or methyl.

In another embodiment of formula (I), $R^6$ is hydrogen.

In an embodiment of formula (I), $R^7$ and $R^8$ are hydrogen.

In an embodiment of, the compound of formula (I) undergoes fast racemization and/or diastereomerization at room temperature.

In an embodiment of formula (I), Z is an achiral moiety.

In another embodiment of formula (I), Z is an aryl or heteroaryl group, wherein the aryl or heteroaryl group may be substituted or unsubstituted.

In an embodiment of formula (I), Z is anthracene, a quinoline-N-oxide, an isoquinoline N-oxide, or a pyridyl N-oxide.

In another embodiment of formula (I), Z is 4'-pyridyl-N-oxide.

In another embodiment of the present invention, the chemosensor compound of formula (I) is a compound of formula (II):

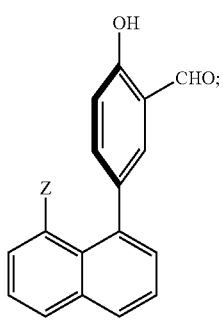

II

Z is a fluorescent moiety, a UV active moiety, or a moiety with fluorescent and UV active properties.

In another embodiment of formula (I), Z is an aryl or heteroaryl group, wherein the aryl or heteroaryl group may be substituted or unsubstituted.

In an embodiment of formula (I), Z is anthracene, a quinoline-N-oxide, an isoquinoline N-oxide, or a pyridyl N-oxide.

In an embodiment of the compound of formula (II) undergoes fast racemization and/or diastereomerization at room temperature.

In an embodiment of the present invention, the chemosensor of formula (I) is a compound of formula 1:

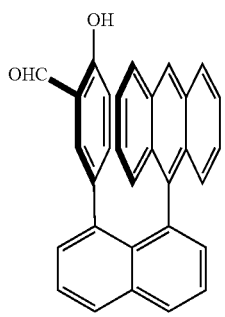

1

In an embodiment of the present invention, the chemosensor of formula (I) is a compound of formula 2:

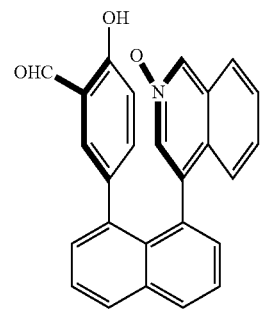

2

In an embodiment of the present invention, the chemosensor compound of formula (I) is a compound of formula 3:

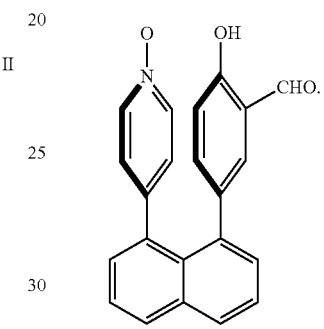

3

In an embodiment of the present invention, a compound of formula (I) may be achiral or chiral. If the compound of formula (I) is chiral, then it may be a present as a racemic mixture, a mixture of stereoisomers, or as a single stereoisomer. In an embodiment, the compound of formula (I) is achiral. In an embodiment where the compound of formula (I) is chiral, the compound of formula (I) may undergo fast racemization and diastereomerization at room temperature.

The present invention also relates to methods of providing stereoselective recognition between chiral substrate compounds of a stereoisomeric mixture, wherein the method comprises of combining a compound of formula (I) with the stereoisomeric mixture, and then isolating the chiral substrate compound as a single stereoisomer.

In another embodiment, the present invention relates to a method for determining the enantiomeric excess of a chiral substrate compound, wherein the method comprises combining a compound of formula (I) with the substrate compound, and then determining the enantiomeric excess of the major stereoisomer by means used by those of skill in the art to determine enantiomeric excess.

In another embodiment, the present invention relates to determining the absolute chemistry of a chiral substrate compound that contains one or more chiral center, wherein the method comprises combining a compound of formula (I) with the substrate compound, and then determining the absolute stereochemistry of the substrate compound by means used by those of skill in the art to determine absolute stereochemistry In another embodiment, the present invention relates to methods for providing the concentration of a compound in a composition, wherein the method comprises combining a compound of formula (I) with the compound, and then determining the concentration of the compound by means used by those of skill in the art.

In an embodiment, each of the analytical methods described herein can be done in a single solution. For example, the compound of formula (I) can be combined with a chiral substrate compound. After the reaction is completed, one or more of the analytical methods described herein can be carried out on the resulting solution without any need to re-combine the compound of formula (I) and the chiral substrate compound. Accordingly, the present invention provides for multifunctional analyses on a single solution.

As described herein, methods for determining the enantiomeric excess and absolute stereochemistry may include UV spectroscopy, circular dichroism (CD) spectroscopy, and fluorescence sensing. Methods for determining substrate concentration may include ultraviolet (UV) spectroscopy and fluorescence sensing.

In an embodiment of this aspect of the invention, a racemic mixture of formula (I) is allowed to react with a chiral compound to form a diastereomeric adduct.

The present invention also relates to a method of providing enantiomeric and/or diastereomeric recognition of a stereoisomer of a chiral compound; wherein the method comprises combining a compound of formula (I) with a sample comprising the chiral substrate compound that may be present as a mixture of stereoisomers, and wherein the compound of formula (I) preferentially binds the stereoisomer to form an adduct.

In some embodiments, the method for providing enantiomeric and/or diastereomeric recognition may further comprise a step for determining the enantiomeric excess (ee) and/or diastereomeric excess (de) of the major stereoisomer of the chiral compound by fluorescence spectroscopy, circular dichroism (CD) spectroscopy, and/or ultraviolet (UV) spectroscopy.

In some embodiments, the method for providing enantiomeric and/or diastereomeric recognition may further comprise a step for determining the total concentration of the stereoisomer by fluorescence spectroscopy or UV spectroscopy.

In some embodiments, the method for providing enantiomeric and/or diastereomeric recognition may further comprise a step for determining the absolute stereochemistry of one or more stereoisomers of a chiral compound by CD spectroscopy, fluorescence spectroscopy, and/or UV spectroscopy.

In some embodiments, the method for providing enantiomeric and/or diastereomeric recognition may comprise the steps of
  (i) Combining a compound of formula (I) with a sample comprising the chiral substrate compound that may be present as a mixture of stereoisomers, and wherein the compound of formula (I) preferentially binds one or more stereoisomers to form an adduct;
  (ii) isolating the adduct from the mixture;
  (iii) cleaving the adduct;
  (iv) separating the compound of formula (I) and the stereoisomer of the chiral compound; and
  (v) isolating the stereoisomer of the chiral compound.

In an embodiment, an adduct formed between compounds of formula (I) and a chiral compound may be cleaved by hydrolysis.

In another embodiment of this aspect of the invention, the chiral substrate compound has an amine, an amide, a carboxylic acid, an amino alcohol, an amino acid, a thiol, an aldehyde, a ketone, or an alcohol function.

In another embodiment of this aspect of the invention, the chiral compound is an amine, an amino alcohol, or an amino acid.

In another embodiment of this aspect of the invention, the chiral compound is an amino alcohol.

In another embodiment of this aspect of the invention, the chiral compound is selected from one or more of the following compounds and stereoisomers or derivatives thereof:

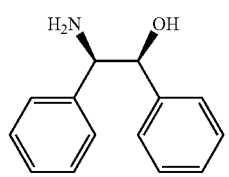

9

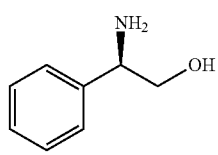

10

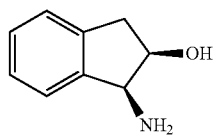

11

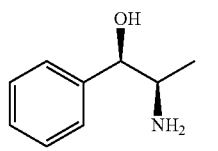

12

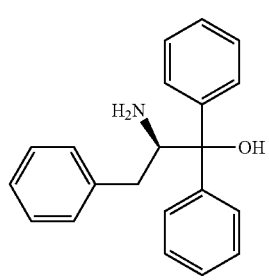

13

14

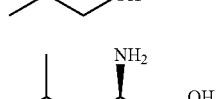

15

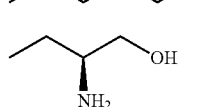

16

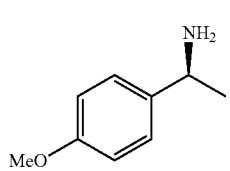

17

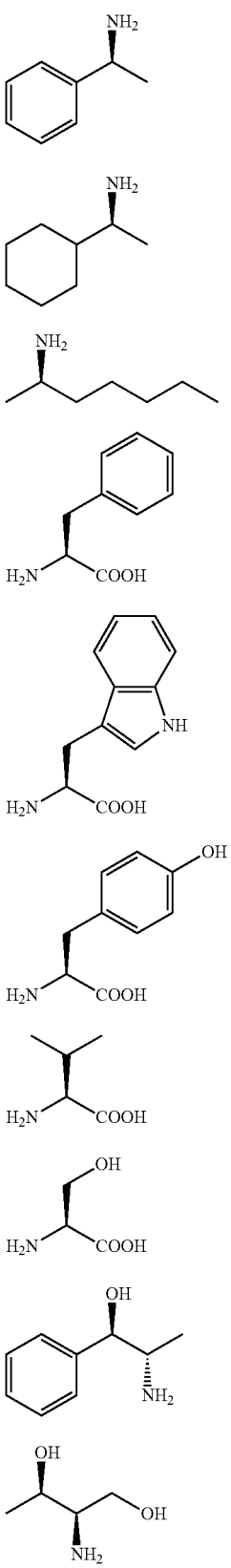

In another embodiment of this aspect of the invention, diastereomeric adducts are formed by condensing a compound of formula (I) with a chiral amine, an amino alcohol, or an amino acid to form an imine product.

In another embodiment of this aspect of the invention, the chiral amino alcohol is selected from the group consisting of 2-amino-1-propanol, 2-amino-4-methyl-1-pentanol, ephedrine or pseudoephedrine.

In another embodiment of this aspect of the invention, the mixture of diastereomeric adducts are heated to allow the interconversion between the diastereomers, which results in a diastereomeric adduct of formula (I) with a % diastereomeric excess (% de) selected from the ranges consisting of ≥50%, ≥60%, ≥70%, ≥80%, ≥90%, ≥95%, ≥98% and ≥99%.

In another embodiment of this aspect of the invention, the diastereomers of the diastereomeric adduct of formula (I) are separated chromatographically, which results in a diastereomeric adduct of formula (I) with a % diastereomeric excess (% de) selected from the ranges consisting of ≥50%, ≥60%, ≥70%, ≥80%, ≥95%, ≥98% and ≥99%.

In another embodiment of this aspect of the invention, the diastereomeric adduct is cleaved to yield a single stereoisomer of a chiral substrate with % enantiomeric excess (% ee) selected from the ranges consisting of ≥50%, ≥60%, ≥70%, ≥80%, ≥90%, ≥95%, ≥98% and ≥99%. Note that ≥99% is effectively complete stereochemical purity.

Another aspect of the invention relates to a method of providing stereoselective recognition between stereoisomers of a chiral compound which comprises of adding a compound of formula (I) to a solution containing a racemic or diastereomeric mixture of the chiral compound.

In one embodiment of this aspect of the invention, the chiral compound is an amine, amino alcohol, amino acid, or an alcohol.

In another embodiment of the invention, the chiral compound is an amine.

In another embodiment of the invention, the chiral amine is selected from the group consisting of 1-phenylethylamine, 3,3-dimethylbutan-2-amine, 3-dimethylbutan-2-amine, cyclohexane-1,2-diamine, 1,2-diphenylethane-1,2-diamine, 1,1-diphenylpropan-2-amine, 1-cyclohexylethanamine, 2,6, 6-trimethylbicyclo[3.1.1]heptan-3-amine, and heptan-2-amine.

Further details related to the aspects and embodiments of the invention follow below.

Due to the lack of bulky substituents close to the aryl-aryl bond, the enantiomers of 3 undergo fast interconversion via *facile* rotation about the stereogenic naphthyl-salicylaldehyde axis at room temperature. This stereodynamic probe has a salicylaldehyde ring capable of fast binding of an amino alcohol and a proximate pyridyl N-oxide fluorophore that reports the binding event.

Figure 2:
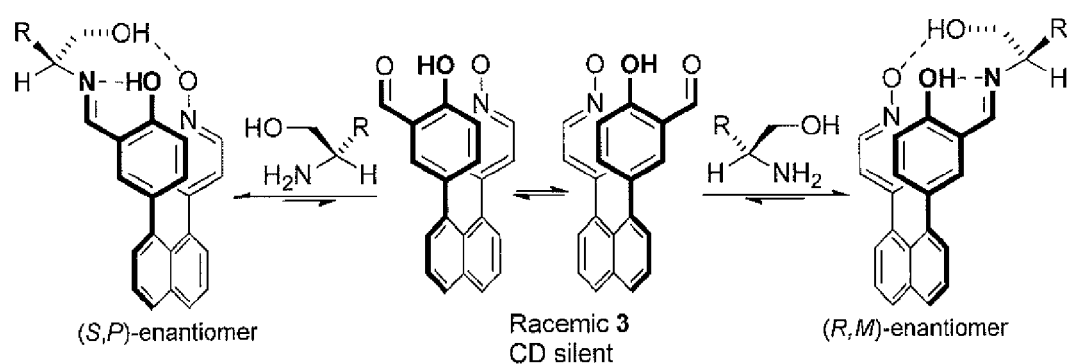
FIG. 2: Anticipated asymmetric induction process upon binding of either an (R)- or (S)-configured amino alcohol locking the sensor into an axially chiral, CD active conformation. Note that the condensation products are enantiomeric and expected to have opposite Cotton effects but identical fluorescence output.

Without being bound by theory, it is assumed that a condensation reaction between a chiral amino alcohol and the reactive formyl group in 3 would lead to a stereochemical bias at the stereogenic axis with characteristic chiroptical output while hydrogen bond interactions between the alcohol moiety of the bound substrate and the N-oxide unit would generate a strong fluorescence response. The design of 3 has several attractive features. First, an adjacent phenol moiety is well known to accelerate the condensation reaction between formyl and amino groups. Second, the imine formation with a chiral amino alcohol was expected to induce population of a single axially chiral conformation of 3 with a distinct CD output (FIG. 2).

This asymmetric transformation of the first kind would be controlled by minimization of steric repulsion and by intramolecular hydrogen bonding between the bound amino alcohol and the neighboring pyridyl N-oxide. Importantly, this process should occur instantaneously due to the rapid rotation about the chiral axis: Third, hydrogen bonding of the alcohol moiety of the substrate to the pyridyl N-oxide group would alter the fluorescence signal of the probe. Altogether, the initially racemic and CD-silent sensor would exhibit (a) an axially chiral conformation with a pronounced chiroptical signal and (b) a change in the fluorescence output. The CD effect would directly correspond to the absolute configuration and ee of the amino alcohol while the fluorescence change would not be enantioselective and therefore provide an entry for the determination of the total concentration of the substrate. Based on the short response time and the inherent sensitivity of fluorescence and CD spectroscopy, the dual readout generated by sensor 3 could then be used for complete stereochemical analysis of minute sample amounts.

Compounds and formula (I) and (II) may be synthesized by methods similar to the exemplary methods for the synthesis of compounds 1, 2, and 3 provided below.

Synthesis of Sensor 1

The synthesis of 1-(3'-formyl-4'-hydroxyphenyl)-8-(9'anthryl)naphthalene, 1, required careful optimization of two consecutive cross-coupling reactions (Scheme 1). Compound 4 can be obtained in 70% yield when the reaction is performed with 7.5 mol % of Pd(PPh$_3$)$_4$ and 5 equivalents of K$_3$PO$_4$ in a toluene:ethanol:water mixture (3:2:1) at 80° C. for four hours. When the subsequent reaction of 4 and anthracene-9-boronic acid was carried out under the same conditions only debromination was observed. However, several changes including an increase in the catalyst loading, reaction time and temperature finally afforded the sterically crowded triaryl 5 carrying two cofacial aryl rings perpendicular to the naphthalene scaffold.[8] The use of LiCl in refluxing DMF produces 1 in 60% yield.[9]

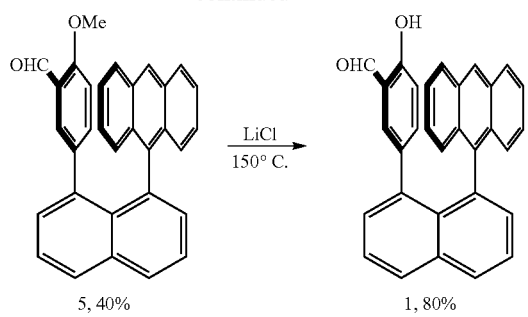

Synthesis of Sensor 2

The experience obtained from the construction of the sterically crowded scaffold of 1 greatly facilitated the synthesis of 2. In this case, however, the fluorophore was introduced first, followed by the attachment of the O-methylated salicylaldehyde unit (Scheme 2). The Suzuki cross-coupling of 1,8-dibromonaphthalene and 4-isoquinolineboronic acid largely left the second carbon-bromide bond intact and gave 26 in 80% yield. Oxidation with m-CPBA in dichloromethane afforded 7, and the second Suzuki coupling of 3-formyl-4-methoxyphenylboronic acid provided 8 in 70% yield. The yields of both coupling steps were significantly higher than the aryl-aryl bond formations leading to compound 1, which can be attributed to the reduced steric hindrance. The crystal structure of 26 also indicates a significantly smaller twisting angle between the bromine and the isoquinolyl ring. The demethylation with BBr$_3$ proceeded smoothly to give 2 under relatively mild conditions.

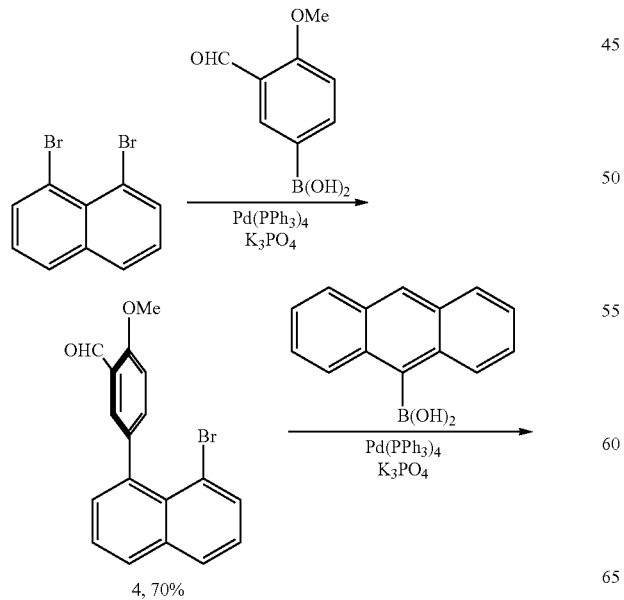

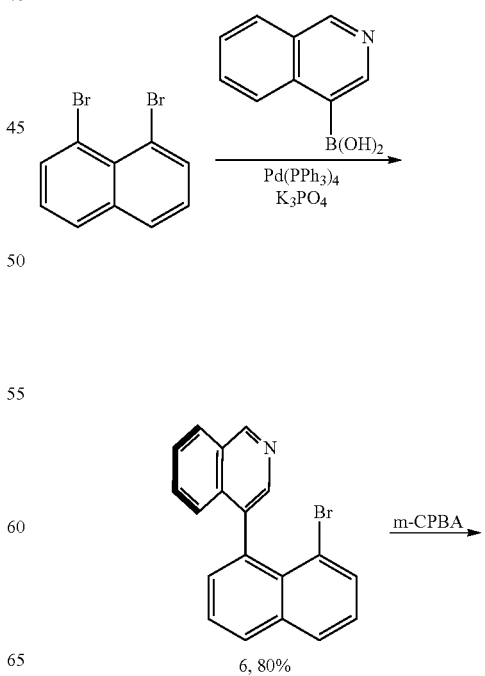

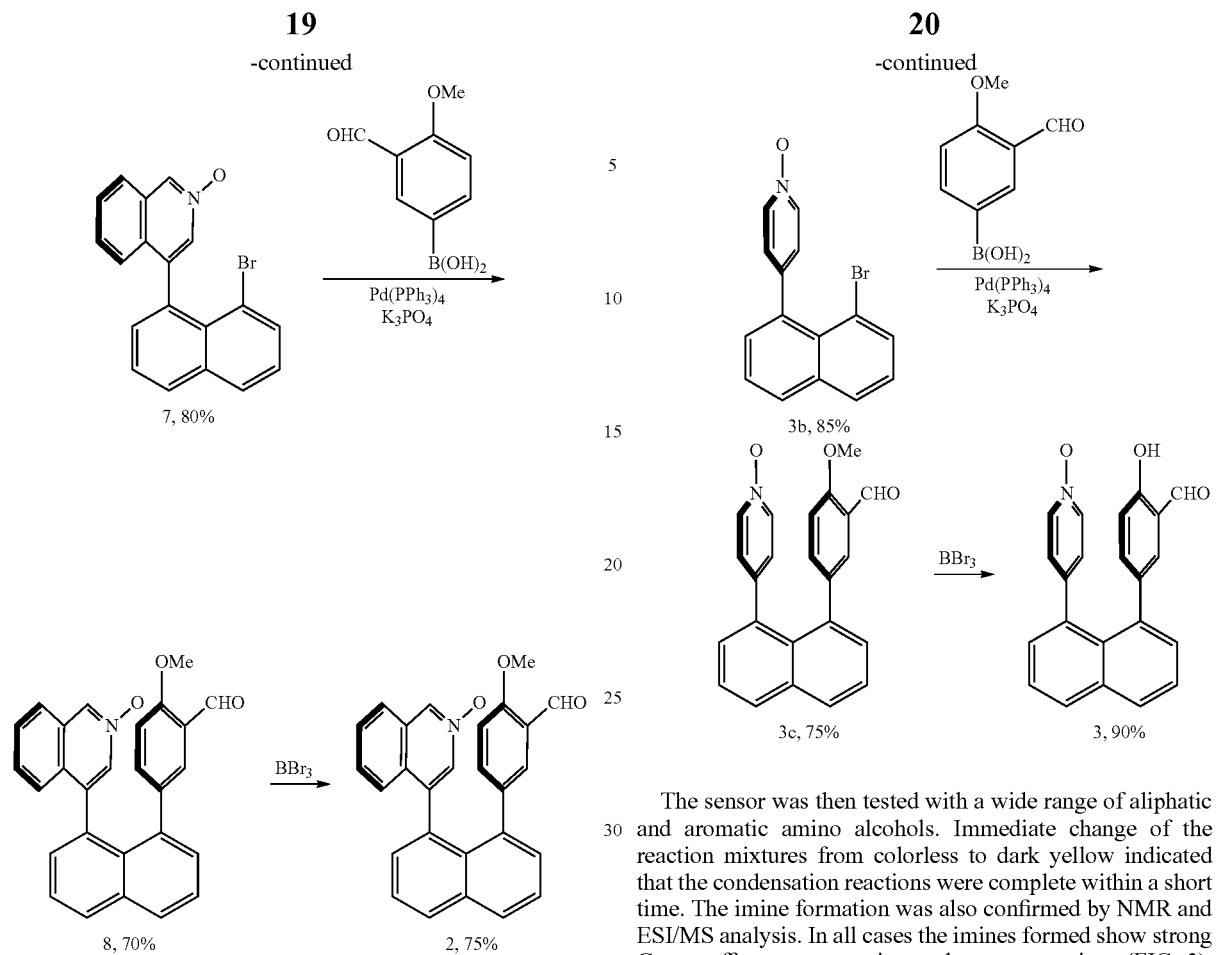

Synthesis of Sensor 3

It was possible to synthesize 3 in four steps from 1,8-dibromonaphthalene (Scheme 3). The selective monoarylation with 4-pyridylphenylbotonic turned out to be very sensitive to temperature, solvent, catalyst loading, equivalents of the boronic acid and reaction time. Through careful optimization of the Suzuki coupling using tetrakis(triphenylphosphine)palladium as catalyst it was possible to develop a procedure that affords 3a in 75% yield, leaving the second aryl bromide function intact. Treatment of 3a with m-CPBA gave N-oxide 3b and a second cross-coupling step provided precursor 3c which was finally deprotected with boron tribromide.

Scheme 3. Synthesis of sensor 3.

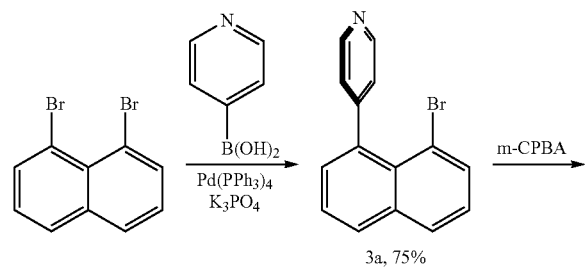

Figure 3:
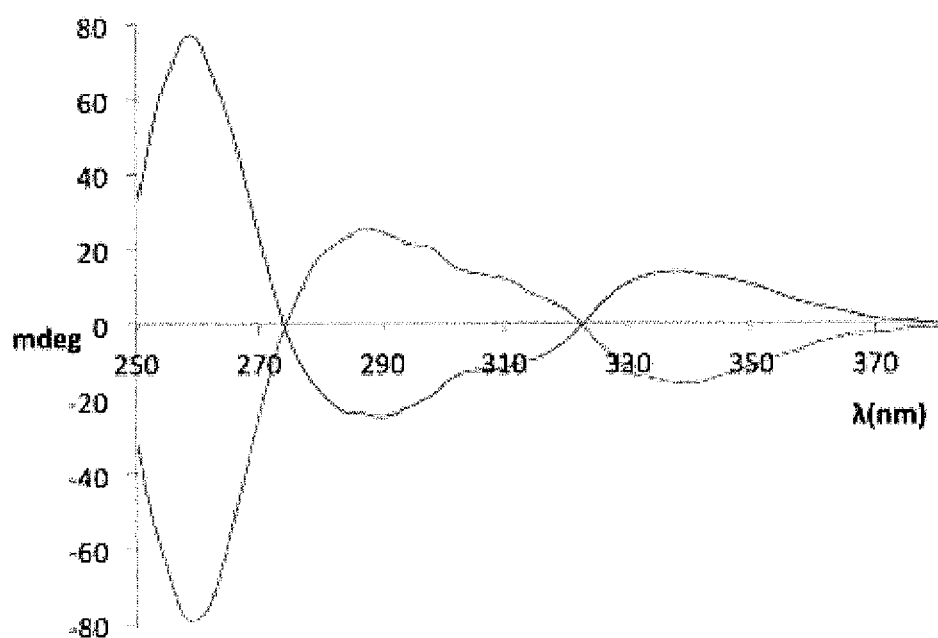
FIG. 3: CD spectra (7.50 10$^{-5}$ M in CHCl$_3$) of the imines formed from 3 and (1S,2R)-9 and (1R,2S)-9 at room temperature.

The sensor was then tested with a wide range of aliphatic and aromatic amino alcohols. Immediate change of the reaction mixtures from colorless to dark yellow indicated that the condensation reactions were complete within a short time. The imine formation was also confirmed by NMR and ESI/MS analysis. In all cases the imines formed show strong Cotton effects even at micromolar concentrations (FIG. 3). Moreover, the chemosensor generates without exception a positive Cotton effect above 330 nm when an acyclic (R)-configured amino group is bound and a negative couplet at the same wavelength when an (S)-configured amine is detected. This is important because it allows one to use 3 for identification of the absolute configuration of amino alcohols.

Figure 4:
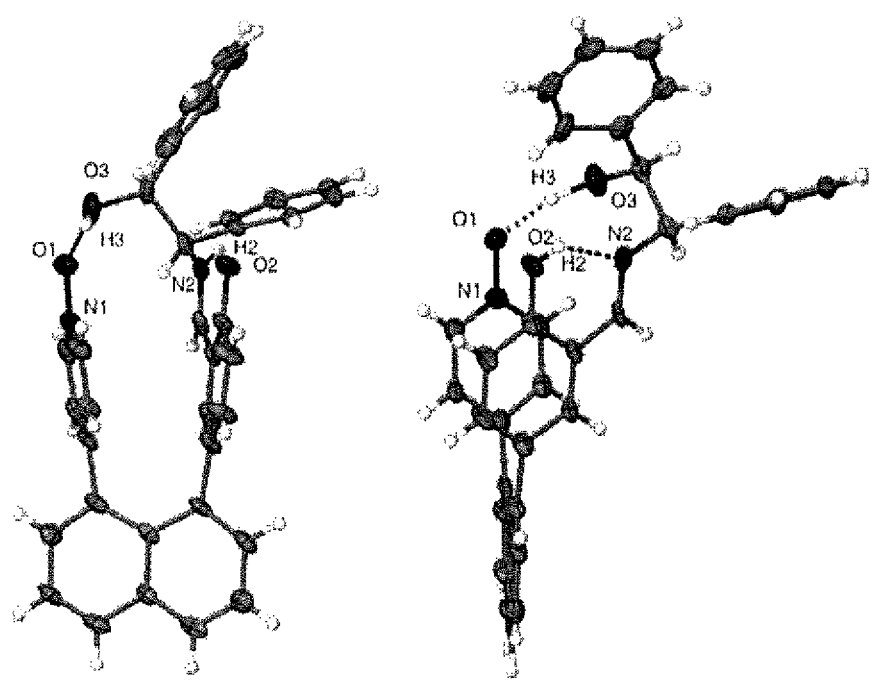
FIG. 4: View facing the naphthalene ring (left) and along the naphthalene ring (right) of the X-ray structure of the (1S,2R,M)-configured imine. Selected crystallographic separations [Å]: O1 . . . H3 1.573, phenyl$_{centroid}$-phenyl$_{centroid}$ 3.338.

It was possible to grow single crystals of the imine derived from 3 and amino alcohol (1S,2R)-9 by slow diffusion of hexanes into a concentrated chloroform solution. Crystallographic analysis proved that the binding of the amino alcohol moiety leads to a stereochemical bias of the chiral axis in 3 as described above. Upon imine formation, the sensor is locked into a structure exhibiting M torsion at the stereogenic aryl-aryl axis which explains the distinct Cotton effects. This central-to-axial chirality induction process is stabilized by hydrogen bonding between the alcohol group and the proximate N-oxide while steric repulsion is kept at a minimum (FIG. 4 and Examples). As a result, the orientation of the salicylidenimine plane with respect to the perpendicular naphthalene ring is controlled by the intramolecular hydrogen bonding motif while the bulky residues of the bound amino alcohol point toward the sterically least hindered direction. The corresponding central-to-axial chirality induction in the stereodynamic sensor thus strongly favors population of a single rigid conformation and an intense CD response.

Figure 5:
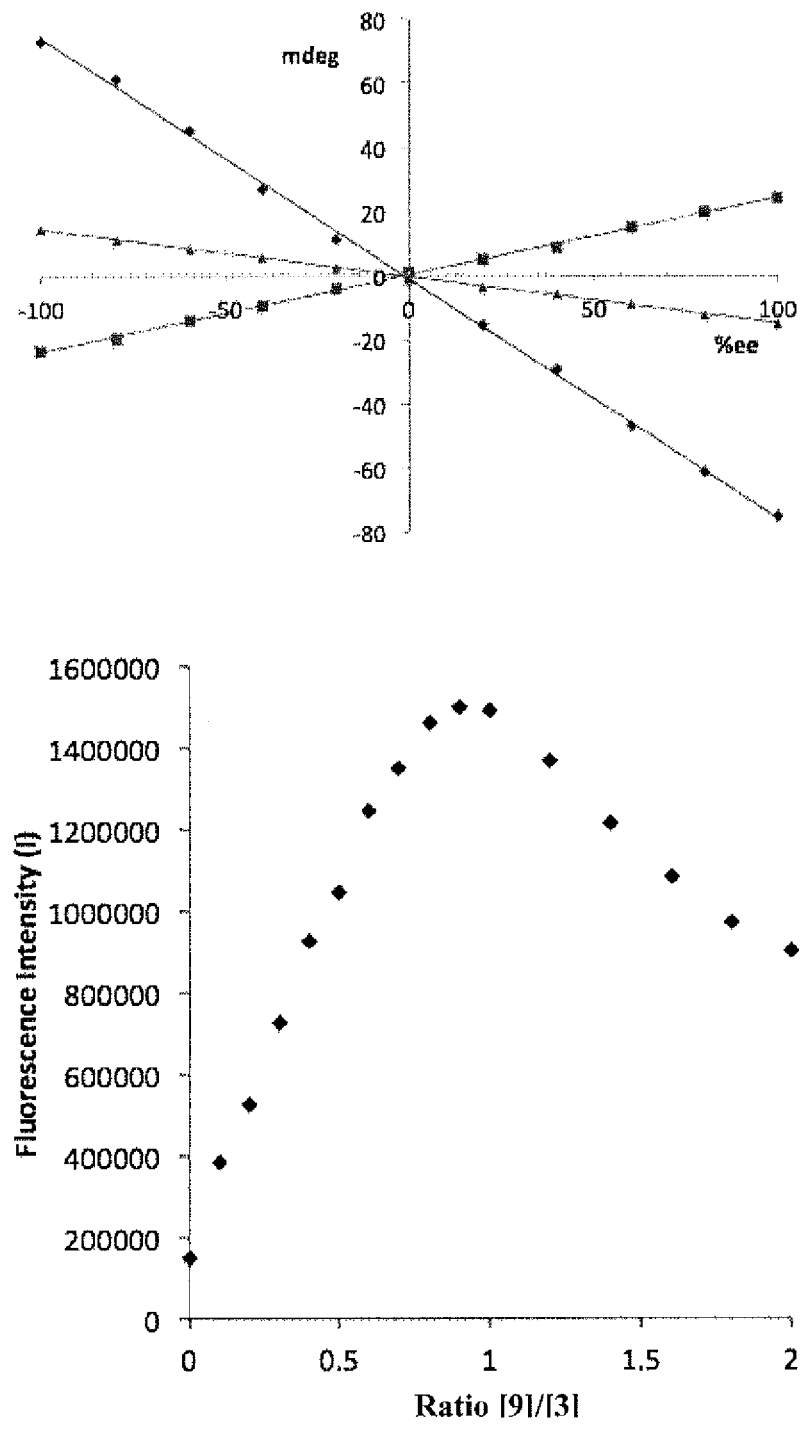
FIG. 5: Top: Plots of the CD maxima at 260, 290, and 340 nm vs. sample ee. Bottom: Plot of the fluorescence intensity at 515 nm vs. ratio [9]/[3].
Figure 6:
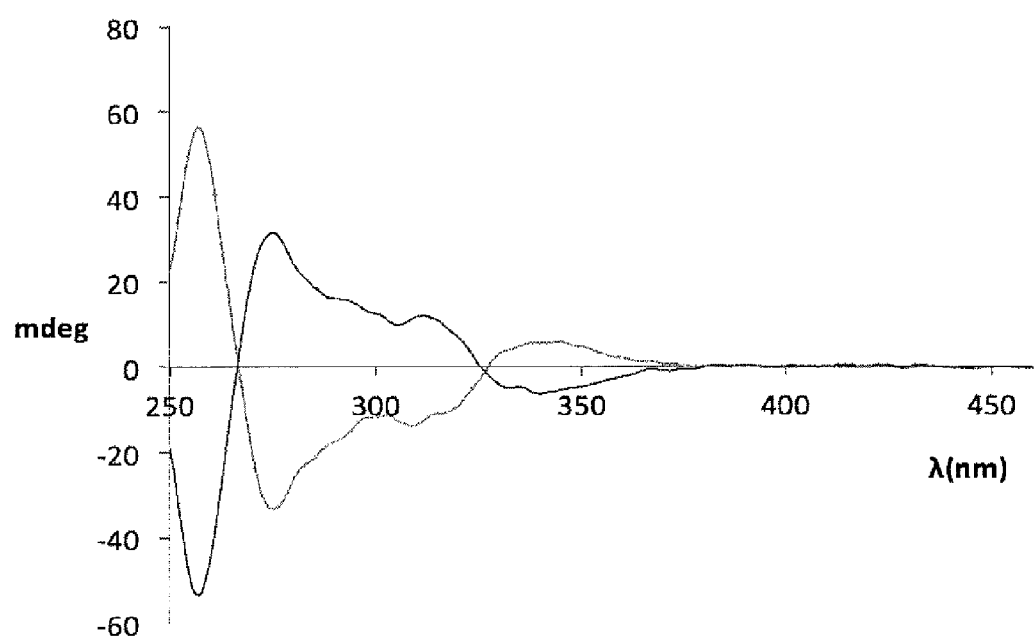
FIG. 6: CD Spectra of the imine obtained from 3 and (R)-15 and (S)-15.
Figure 7:
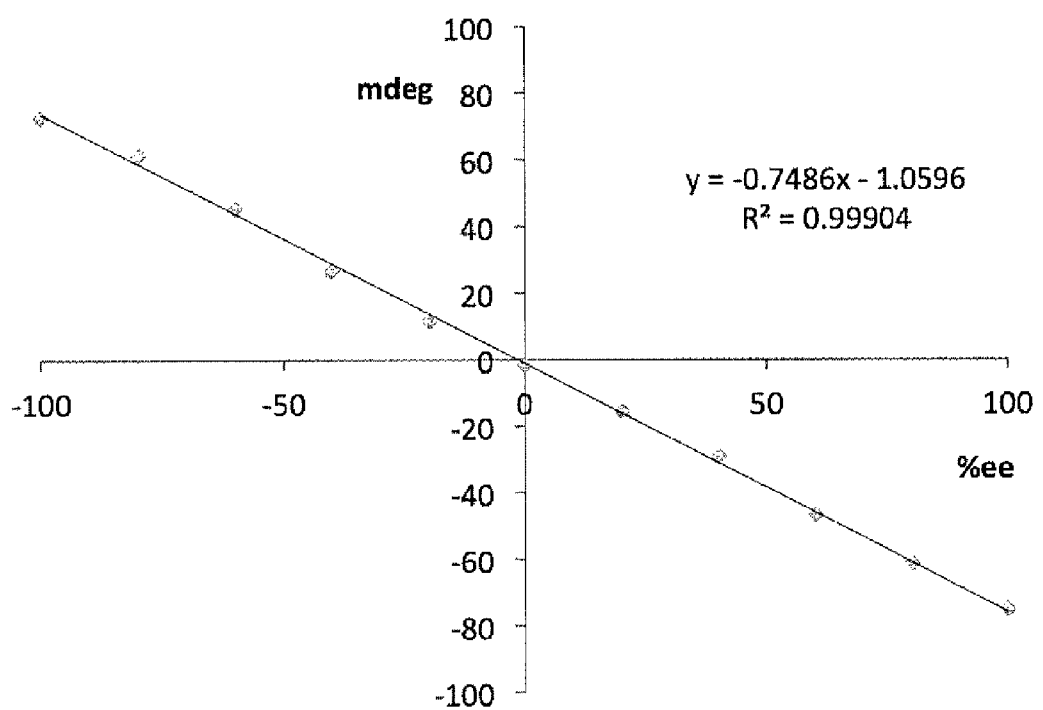
FIG. 7: Linear relationship between the CD amplitude at 260 nm and the enantiomeric excess of 9 using chemosensor 3.
Figure 8:
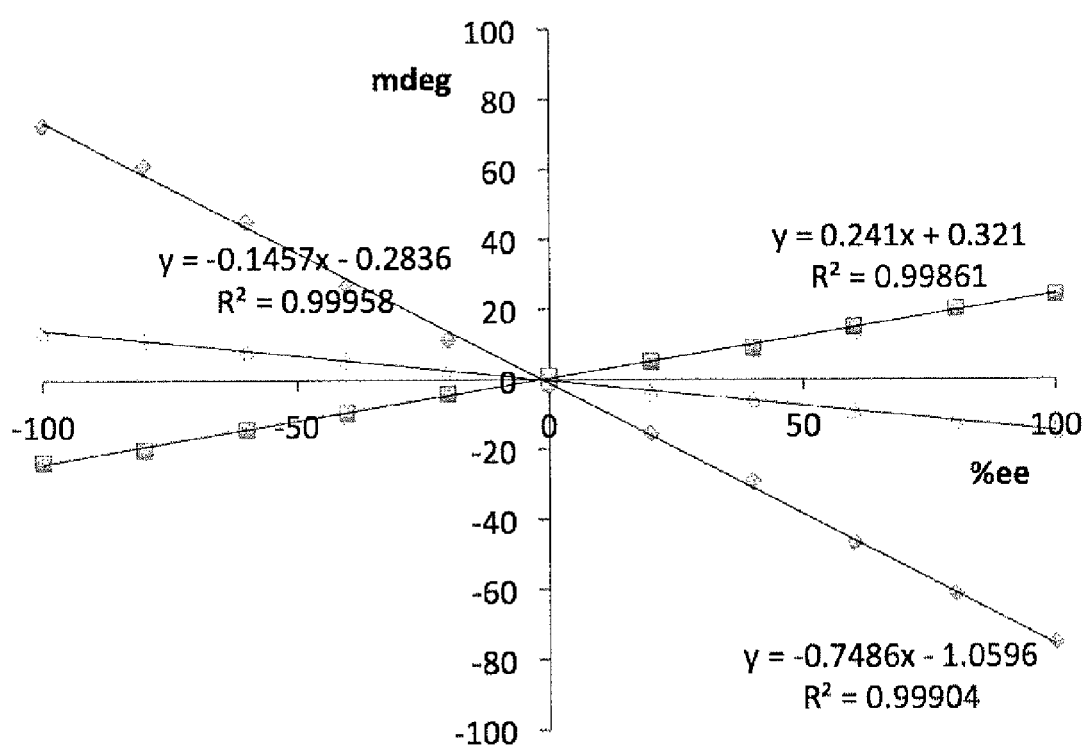
FIG. 8: Calibration curves generated from CD amplitudes at 260 (diamond), 290 (square), and 340 (triangle) nm for the enantiomeric excess of 9 using chemosensor 3.
Figure 9:
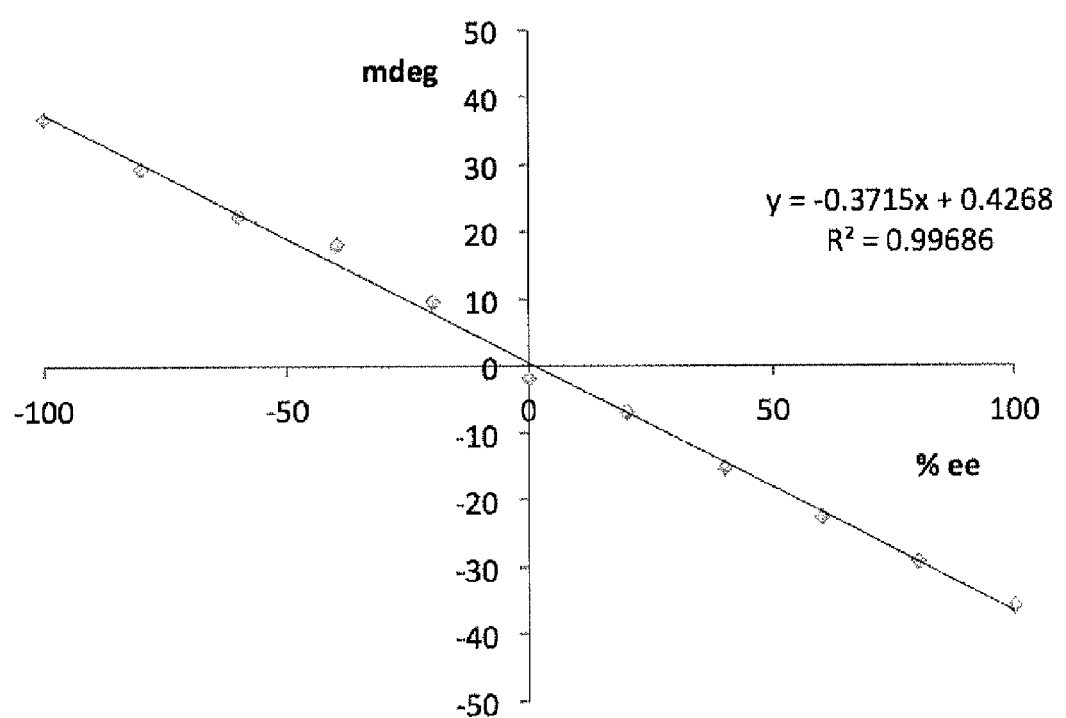
FIG. 9: Linear relationship between the CD amplitude at 275 nm and the enantiomeric excess of 16 using chemosensor 3.
Figure 10:
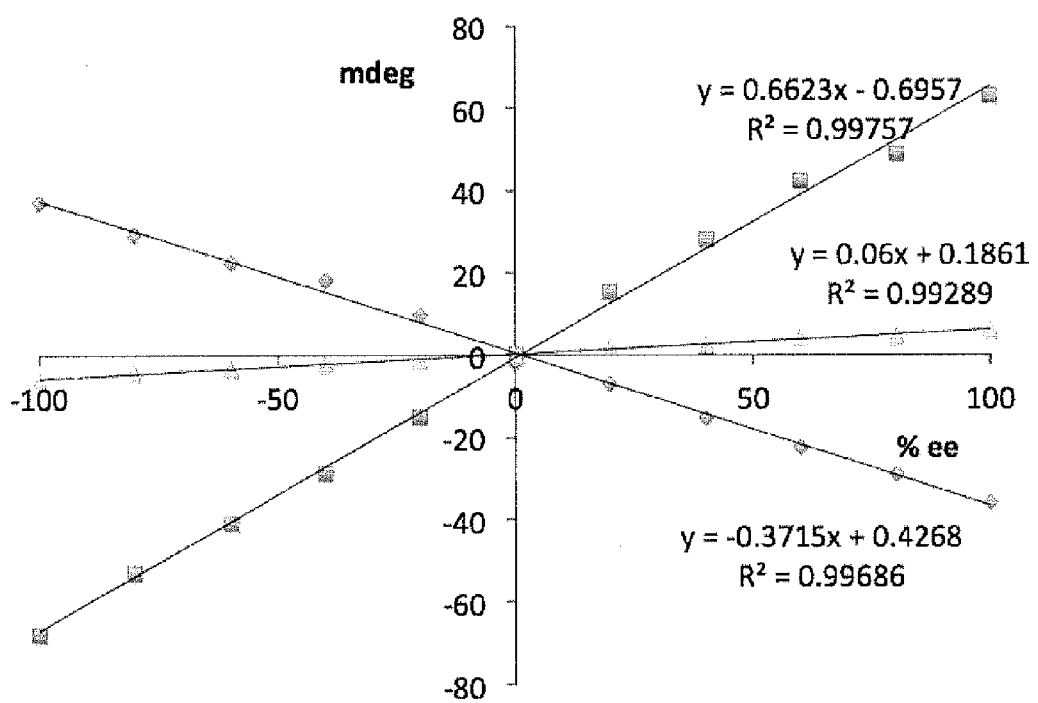
FIG. 10: Calibration curves generated from CD amplitudes at 257 (square), 275 (diamond), and 340 (triangle) nm of 16 using chemosensor 3.
Figure 11:
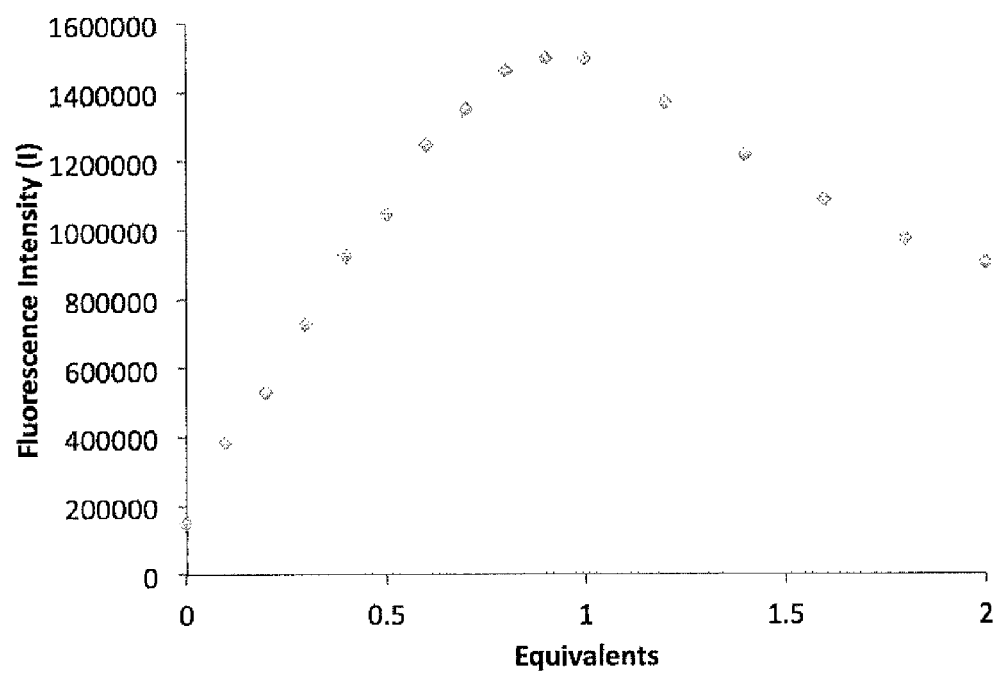
FIG. 11: Fluorescence intensity (f) measured at 515 nm plotted against equivalents of 9 using chemosensor 3.
Figure 12:
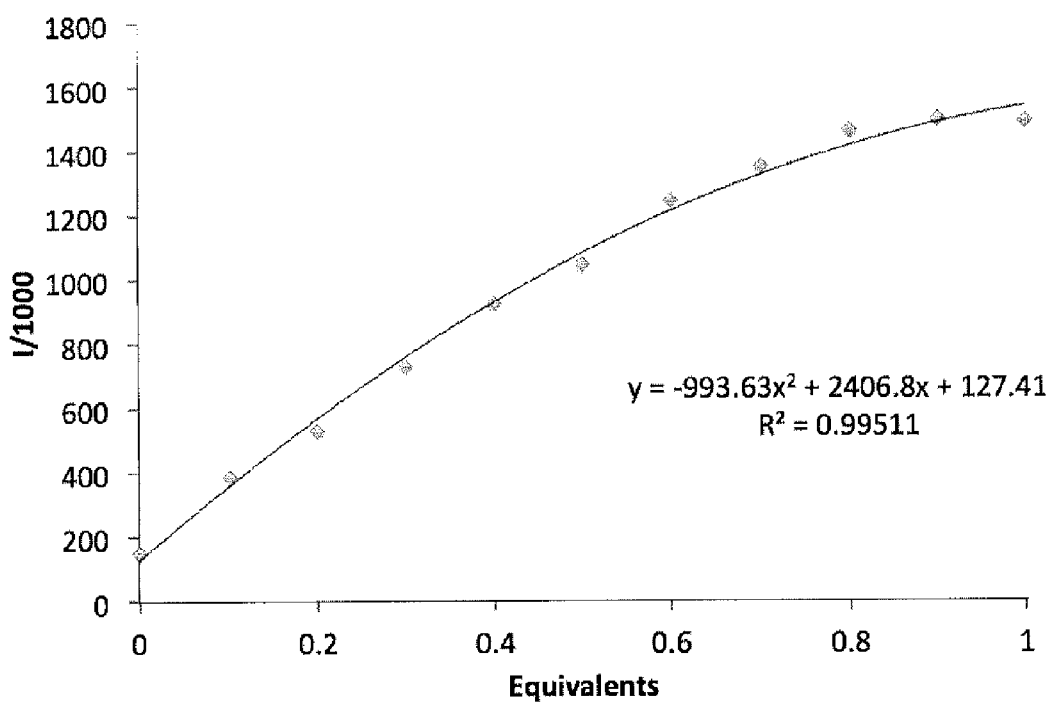
FIG. 12: Curve fitting of the fluorescence emission at 515 nm plotted against equivalents of 9 using chemosensor 3.
Figure 13:
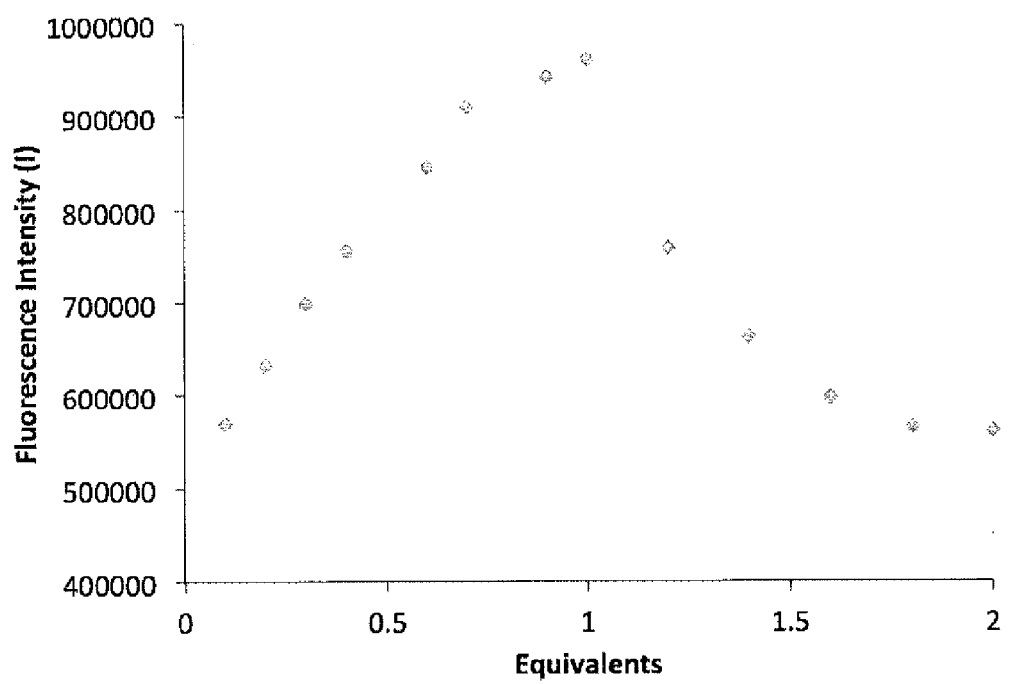
FIG. 13: Fluorescence intensity (I) measured at 430 nm plotted against equivalents of 16 using chemosensor 3.
Figure 14:
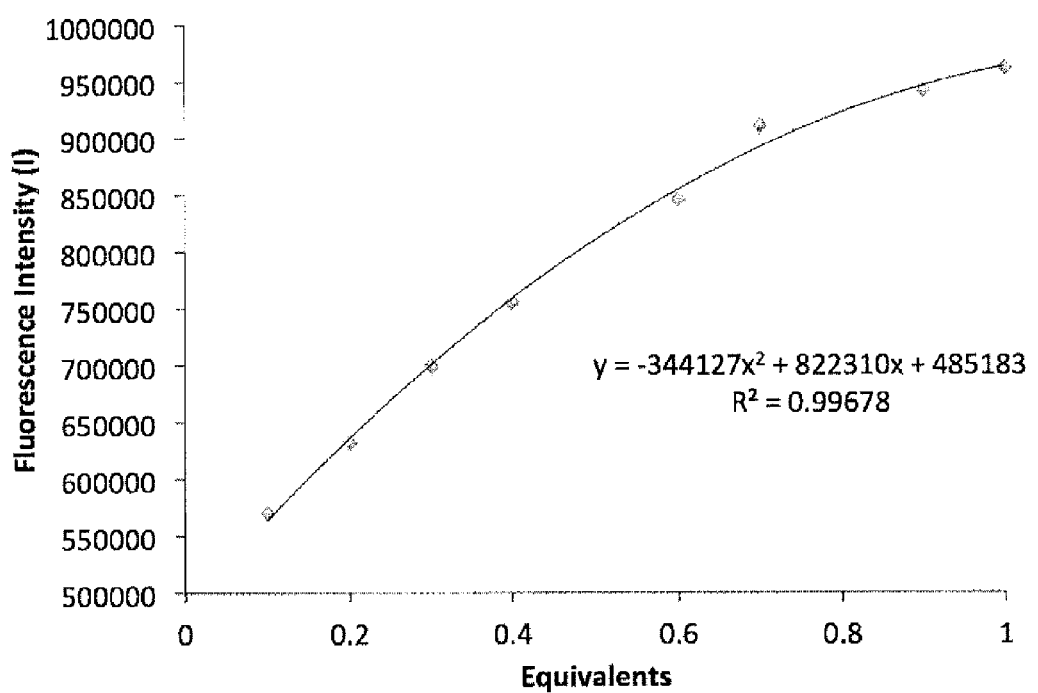
FIG. 14: Curve fitting of the fluorescence emission at 430 nm plotted against equivalents of 16 using chemosensor 3.
Figure 15:
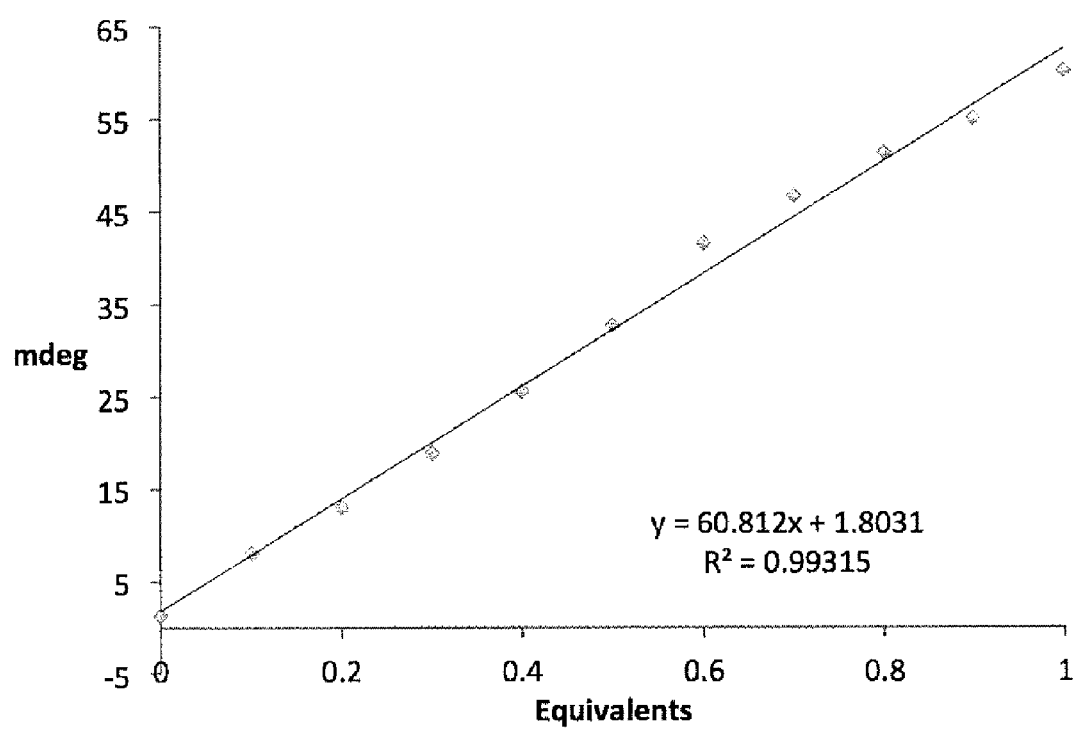
FIG. 15: CD amplitude at 260 nm of the imine versus the number of molar equivalents of 9 using chemosensor 3.
Figure 16:
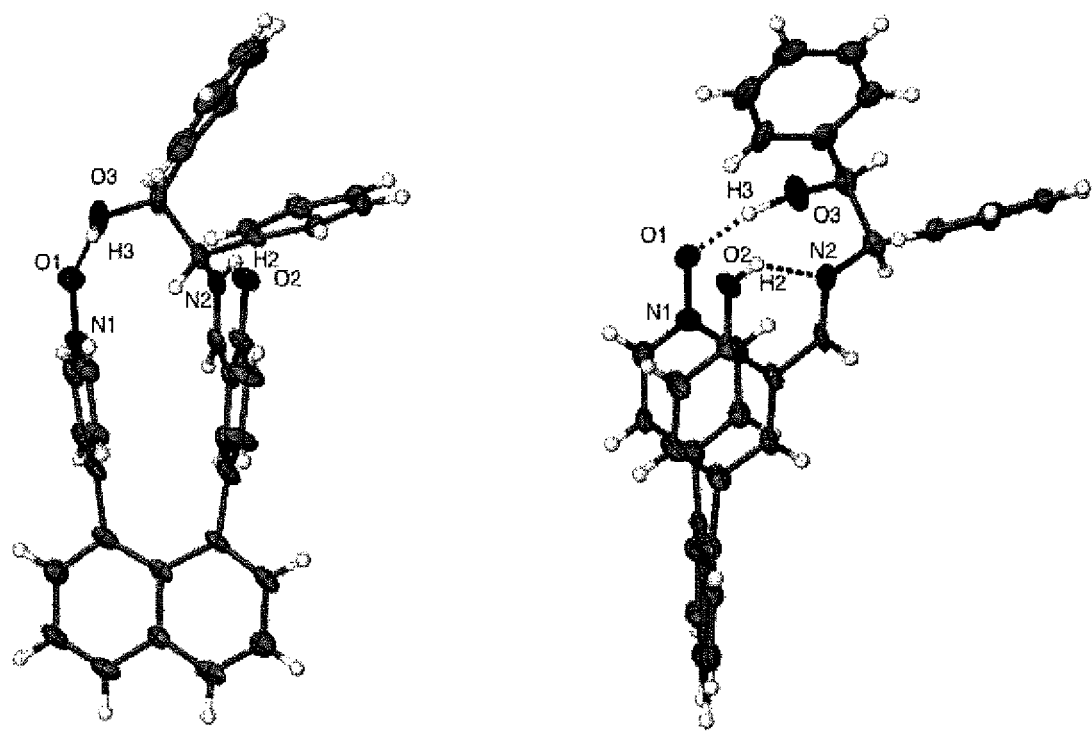
FIG. 16: Imine A from substrate 9 with chemosensor 3: View facing the naphthalene ring (left) and along the naphthalene ring (right).
Figure 17:
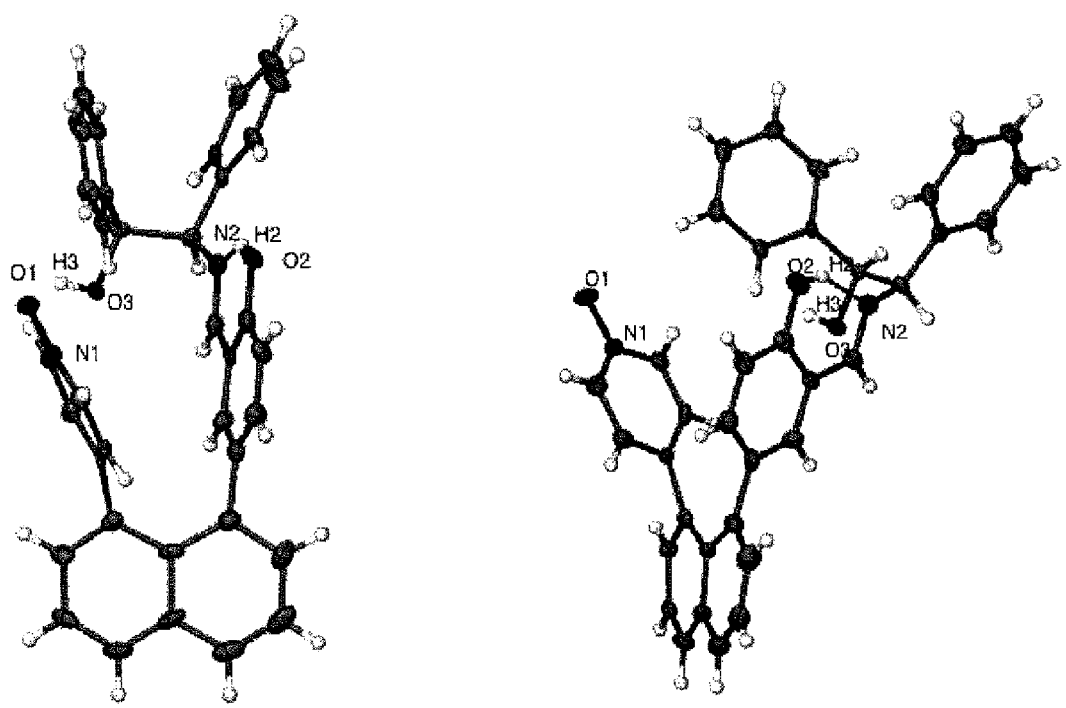
FIG. 17: Imine B from substrate 9 with chemosensor 3: View facing the naphthalene ring (left) and along the naphthalene ring (right).
Figure 18:
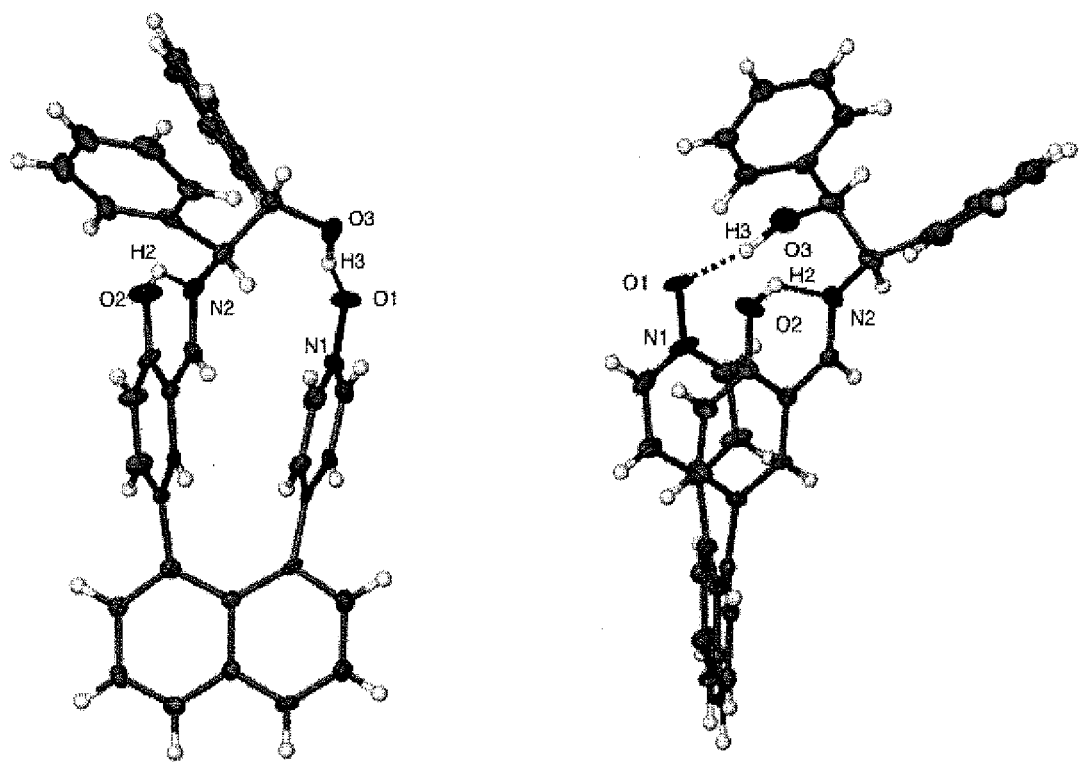
FIG. 18: Imine C from substrate 9 with chemosensor 3: View facing the naphthalene ring (left) and along the naphthalene ring (right).
Figure 19:
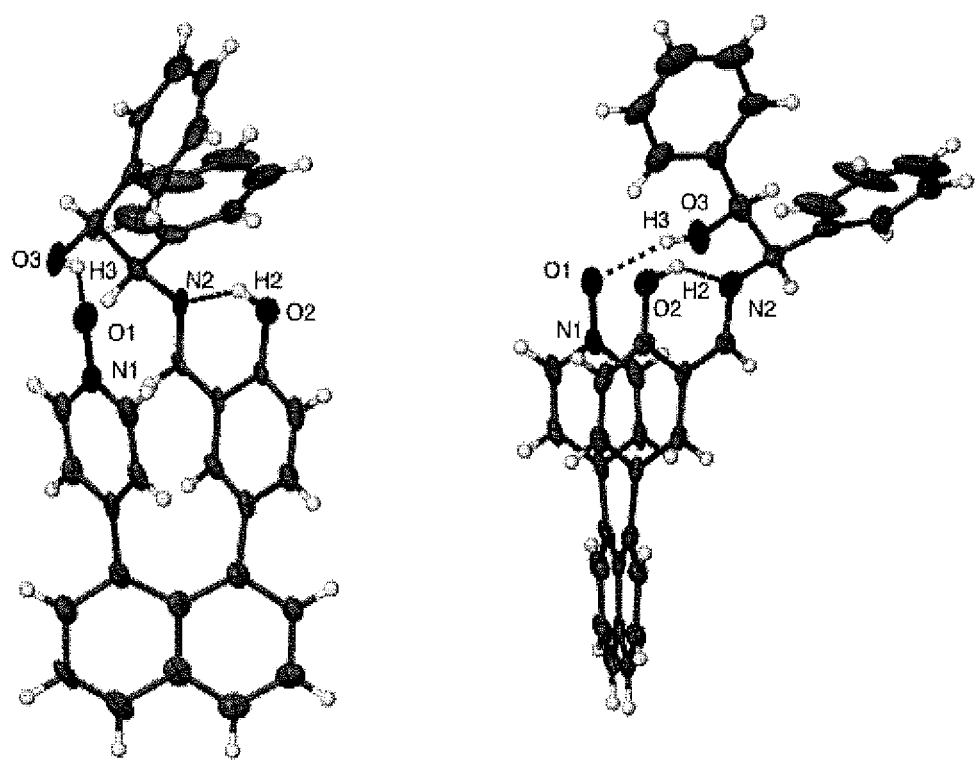
FIG. 19: Imine D from substrate 9 with chemosensor 3: View facing the naphthalene ring (left) and along the naphthalene ring (right).

The CD spectra were collected of scalemic samples of the imines obtained with 9 and 16, respectively, to evaluate the practical use of 3 for quantitative ee determination (FIG. 5). In both cases, a perfectly linear relationship between the CD response of 3 and the sample ee were found (see Examples).

Five scalemic samples of 9 covering a wide ee range were prepared and treated with sensor 3 at room temperature. Using the linear regression equation calculated from the calibration curve and the measured CD amplitudes at 260 nm, the experimentally determined enantiomeric excess of these samples was within 2% of the actual values. Similar results were obtained with scalemic samples of 16 (Examples).

Having established the nature of the chiral induction process and the use of 3 for quantitative ee determination of amino alcohols, the effect of the substrate binding on the fluorescence response of 3 was investigated. Imine formation results in a strong increase in the fluorescence intensity until more than one equivalent of the amino alcohol is added (FIG. 5 and Examples). While the fluorescence enhancement can be attributed to the formation of a rigid structure stabilized by intramolecular hydrogen bonding, the decrease in the fluorescence intensity observed in the presence of unbound substrate is probably a result of dynamic quenching. In accordance to the ee determination discussed above, the fluorescence change of 3, i.e. a steady fluorescence increase that is followed by quenching when excess of an amino alcohol is present, is a general phenomenon and has been used for accurate quantification of the concentration of 9 and 16 (Examples). Regression analysis of five samples containing various amounts of amino alcohol 9 demonstrated that the total amount can be determined within a 2.5% error margin.

Finally, the independent CD and fluorescence readout of 3 was used to achieve a full stereochemical analysis of scalemic mixtures at once, i.e. the determination of the absolute configuration of the major enantiomer, the ee and the total substrate concentration. Four samples with varying concentration and enantiomeric composition of 9 were analyzed as described above (Table 1 and Examples). The results obtained by our dual sensing method deviated less than 5% from the actual values. The accuracy of the analysis performed with 3 is generally considered sufficient for HTS purposes and it compares well with previously reported optical ee measurements obtained using two probes simultaneously or in tandem. The optical measurements are operationally simple, fast and require only small sample and solvent amounts. In all experiments, the reaction mixtures were analyzed directly. The general simplicity and exclusion of any purification steps underscores the practicality of chemosensing with 3.

TABLE 1

Complete stereochemical analysis of 9.

| Sample Composition | | | Sensing Results | | |
|---|---|---|---|---|---|
| Conc. (mM) | Ee (%) | Abs. Config.[a] | Conc. (mM) | Ee (%) | Abs. Config.[a] |
| 1.20 | 28.0 | 1S,2R | 1.21 | 24.8 | 1S,2R |
| 2.14 | 10.0 | 1S,2R | 1.97 | 13.7 | 1S,2R |
| 2.70 | 52.0 | 1R,2S | 2.65 | 52.9 | 1R,2S |
| 3.04 | 64.0 | 1R,2S | 3.00 | 62.4 | 1R,2S |

[a]Major enantiomer

A versatile chemosensor 3 that can be used for in-situ determination of the absolute configuration, ee and concentration of chiral compounds based on a dual mode readout has been developed. This stereodynamic probe produces a distinct CD signal upon condensation with amino alcohols that can be correlated to the substrate chirality and enantiomeric composition while the independent fluorescence response is not enantioselective and allows quantification of the total amount. Screening of several amino alcohols showed that 3 has a broad substrate scope. The analysis is accurate, avoids time-consuming work-up and purification steps, and it is applicable to minute sample amounts which reduces the use of solvents and waste production. Finally, it is notable that 3 is used in racemic form which eliminates the general need for asymmetric production of enantiopure sensors previously employed in HTS analysis of chiral compounds.

EXAMPLES

1. Synthetic Procedures

All reagents and solvents were commercially available and used without further purification. Reactions were carried out under inert and anhydrous conditions. Flash chromatography was performed on silica gel, particle size 40-63 μm. NMR spectra were obtained at 400 MHz ($^1$H-NMR) and 100 MHz ($^{13}$C-NMR) using $CDCl_3$ as solvent and TMS as reference. Electrospray ionization mass spectra (ESI-MS) were collected with samples dissolved in chloroform/methanol (1:1, 0.5 mg/mL).

Synthesis of 1-(3'-formyl-4'-hydroxyphenyl)-8-(9'-anthryl)naphthalene (1) and Product Characterization

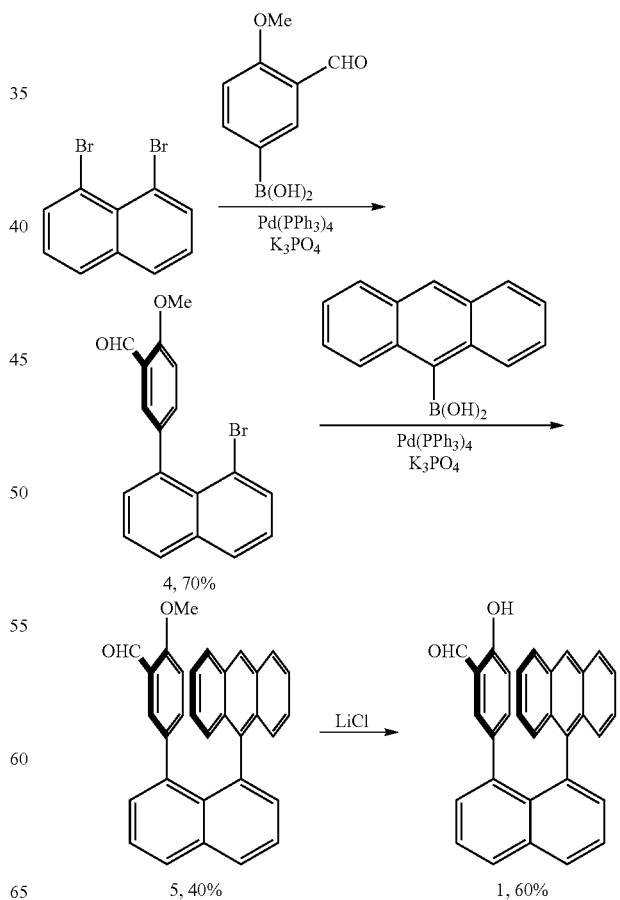

1-(3'-Formyl-4'-methoxyphenyl)-8-bromonaphthalene (4)

A solution of 1,8-dibromonaphthalene (500 mg, 1.7 mmol), 3-formyl-4-methoxyphenylboronic acid (472.0 mg, 2.6 mmol), Pd(PPh$_3$)$_4$ (151.5 mg, 0.13 mmol), and K$_3$PO$_4$ (927.7 mg, 4.4 mmol) in 18 mL of toluene:ethanol:water (3:2:1 v/v) was stirred at 80° C. for 4 hours. The resulting mixture was allowed to cool to room temperature, quenched with water, and extracted with CH$_2$Cl$_2$. The combined organic layers were dried over MgSO$_4$ and concentrated in vacuo. Purification by flash chromatography on silica gel (CH$_2$Cl$_2$:hexanes 4:1) afforded 417 mg (1.2 mmol, 70% yield) of a yellow solid.

$^1$H NMR δ =4.02 (s, 3H), 7.12 (d, J=8.5 Hz, 1H), 7.39-7.50 (m, 3H), 7.68 (d, J=8.2 Hz, 1H), 7.81 (dd, J=8.4 Hz, 8.2 Hz, 2H), 7.90 (d, J=8.0 Hz, 1H), 7.98 (s, 1H), 10.56 (s, 1H). $^{13}$C NMR: δ=55.8, 110.7, 119.8, 124.0, 125.3, 126.1, 129.0, 129.1, 129.5, 129.8, 131.4, 133.8, 135.3, 136.1, 137.4, 138.6, 161.1, 190.0. Anal. Calcd. C$_{18}$H$_{13}$BrO$_2$: C, 63.36; H, 3.84. Found: C, 63.18; H, 4.06.

1-(3'-Formyl-4'-methoxyphenyl)-8-(9'-anthryl)naphthalene (5)

A solution of 3 (400 mg, 1.2 mmol), anthracene-9-boronic acid (390 mg, 1.8 mmol), Pd(PPh$_3$)$_4$ (208 mg, 0.2 mmol), and K$_3$PO$_4$ (636.8 mg, 3.0 mmol) in 15 mL of toluene was stirred at 120° C. for 18 hours. The resulting mixture was allowed to cool to room temperature, quenched with water, and extracted with CH$_2$Cl$_2$. The combined organic layers were dried over MgSO$_4$ and concentrated in vacuo. Purification by flash chromatography on silica gel (CH$_2$Cl$_2$: hexanes 4:1) afforded 206 mg (0.5 mmol, 40% yield) of a yellow solid.

$^1$H NMR: δ=3.61 (s, 3H), 5.53 (d, J=8.5 Hz, 1H), 6.30 (dd, J=8.5 Hz, 2.2 Hz, 1H), 6.63 (d, J=2.1 Hz, 1H), 7.08 (d, J=7.0 Hz, 1H), 7.20-7.41 (m, 7H), 7.49 (dd, J=7.7 Hz, 7.5 Hz, 1H), 7.63 (dd, J=7.8 Hz, 7.4 Hz, 1H), 7.78 (d, J=8.5 Hz, 1H), 7.84 (d, J=8.5 Hz, 1H), 8.05-8.08 (m, 2H), 8.11 (d, J=8.2 Hz, 1H), 9.63 (s, 1H), $^{13}$C NMR: δ=55.3, 108.0, 121.4, 124.7, 125.0, 125.1, 125.3, 125.4, 125.7, 125.9, 126.9, 127.1, 127.7, 127.8, 127.9, 129.2, 129.4, 130.0, 130.7, 130.9, 131.2, 131.3, 131.8, 132.0, 133.8, 134.7, 135.0, 135.6, 137.5, 139.1, 158.8, 188.4. Anal. Calcd. C$_{32}$H$_{22}$O$_2$: C, 87.65; H, 5.06. Found: C, 87.85; H, 5.27.

1-(3'-Formyl-4'-hydroxyphenyl)-8-(9'-anthryl)naphthalene (1)

A solution of 4 (200 mg, 0.46 mmol) and LiCl (193 mg, 4.6 mmol) in 5 mL of DMF was stirred at 150° C. for 12 hours. The resulting mixture was allowed to cool to room temperature, quenched with water and extracted with CH$_2$Cl$_2$. The combined organic layers were washed with brine, dried over MgSO$_4$ and concentrated in vacuo. Purification by flash chromatography on silica gel (CH$_2$Cl$_2$: hexane 2:1) afforded 87.1 mg (0.2 mmol, 60% yield) of a yellow solid.

$^1$H NMR: δ=5.65 (d, J=8.4 Hz, 1H), 6.26 (d, J=2.2 Hz, 1H), 6.30 (dd, J=8.4 Hz, 2.3 Hz, 1H), 7.07 (d, J=7.0 Hz, 1H), 7.19-7.38 (m, 5H), 7.44 (d, J=8.3 Hz, 1H), 7.48-7.53 (m, 2H), 7.66 (dd, J=8.1 Hz, 8.0 Hz, 1H), 7.81 (ddd, J=8.6 Hz, 8.5 Hz, 2.9 Hz, 2H), 8.06 (d, J=8.3 Hz, 1H), 8.11-8.14 (m, 2H), 8.56 (s, 1H), 10.42 (s, 1H). $^{13}$C NMR: δ=113.7, 117.2, 124.8, 124.9, 125.0, 125.2, 125.4, 125.5, 126.0, 126.7, 127.1, 128.4, 128.5, 129.4, 129.5, 130.2, 130.8, 130.9, 131.2, 131.3, 131.8, 132.1, 132.3, 132.9, 135.0, 135.1, 135.5, 137.4, 138.8, 158.9, 195.6. Anal. Calcd. C$_{31}$H$_{20}$O$_2$: C, 87.71; H, 4.75. Found: C, 87.97; H, 5.08.

Synthesis of 1-(4'-isoquinolyl)-8-(3'-formyl-4'-hydroxyphenyl)naphthalene N-oxide (2) and Product Characterization

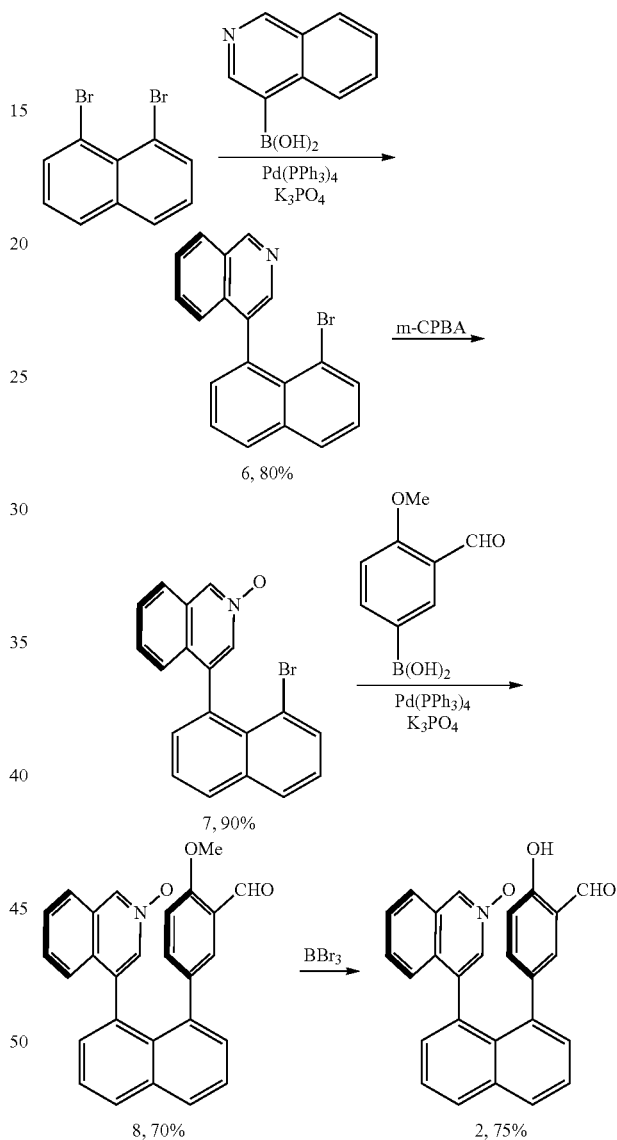

1-Isoquinolyl-8-bromonaphthalene (6)

A solution of 1,8-dibromonaphthalene (500 mg, 1.7 mmol), 4-isoquinolineboronic acid (453.7 mg, 2.6 mmol), Pd(PPh$_3$)$_4$ (151.5 mg, 0.13 mmol), and K$_3$PO$_4$ (927.7 mg, 4.4 mmol) in 18 mL of toluene:ethanol:water (3:2:1 v/v) was stirred at 80° C. for 4 hours. The resulting mixture was allowed to cool to room temperature, quenched with water, and extracted with CH$_2$Cl$_2$. The combined organic layers were dried over MgSO$_4$ and concentrated in vacuo. Purification by flash chromatography on silica gel (CH₂Cl₂:EtOAc 2:1) afforded 470 mg (1.4 mmol, 80% yield) of a yellow solid.

¹H NMR: δ=7.26-7.36 (m, 2H), 7.51-7.61 (m, 4H), 7.71 (d, J=7.4 Hz, 1H), 7.95 (d, J=8.0 Hz, 1H), 8.01 (dd, J=9.3 Hz, 9.3 Hz, 2H), 8.48 (s, 1H), 9.33 (s, 1H). ¹³C NMR: δ=119.7, 125.2, 125.5, 126.4, 127.0, 127.5, 127.8, 129.2, 130.1, 130.3, 130.6, 132.1, 133.9, 134.0, 134.2, 136.0, 136.6, 143.2, 151.7. Anal. Calcd. C₁₉H₁₂BrN: C, 68.28; H, 3.62; N, 4.19. Found: C, 68.07; H, 3.62; N, 4.13.

1-(4'-Isoquinolyl)-8-bromonaphthalene N-oxide (7)

A solution of 5 (470 mg, 1.4 mmol) and m-CBPA (728 mg, 4.2 mmol) in 15 mL of CH₂Cl₂ was stirred at room temperature for 12 hours. The mixture was washed with 2M NaOH, dried over MgSO₄, and concentrated in vacuo. Purification by flash chromatography on silica gel (CH₂Cl₂:MeOH 20:1) afforded 441 mg (1.26 mmol, 90% yield) of a light brown solid.

¹H NMR: δ=7.14 (d, J=8.5 Hz, 1H), 7.34-7.42 (m, 2H), 7.48 (d, J=7.1 Hz, 1H), 7.56-7.62 (m, 2H), 7.75 (d, J=7.6 Hz, 1H), 7.77 (d, J=8.4 Hz, 1H), 7.96 (d, J=8.6 Hz, 1H), 8.05 (d, J=8.9 Hz, 1H), 8.16 (s, 1H), 8.85 (s, 1H). ¹³C NMR: δ=119.2, 125.0, 125.5, 126.8, 128.9, 128.9, 129.2, 129.3, 130.1, 130.9, 131.1, 131.1, 131.9, 134.2, 135.3, 135.9, 136.9, 138.8. Anal. Calcd. C₁₉H₁₂BrNO: C, 65.16; H, 3.45; N, 4.00. Found: C, 65.14; H, 3.75; N, 3.84.

1-(4'-Isoquinolyl)-8-(3'-formyl-4'-methoxyphenyl)naphthalene N-oxide (8)

A solution of 6 (440 mg, 1.3 mmol), 3-formyl-4-methoxyphenylboronic acid (339.2 mg, 1.9 mmol), Pd(PPh₃)₄ (109 mg, 0.1 mmol) and K₃PO₄ (669 mg, 3.2 mmol) in 18 mL of toluene:ethanol:water (3:2:1 v/v) was stirred at 100° C. for 12 hours. The resulting mixture was allowed to cool to room temperature, quenched with water, and extracted with CH₂Cl₂. The combined organic layers were dried over MgSO₄ and concentrated in vacuo. Purification by flash chromatography on silica gel (CH₂Cl₂:MeOH 20:1) afforded 357.6 mg (0.88 mmol, 70% yield) of a light brown solid. NMR analysis showed a mixture of syn and anti isomers with a ratio of 80:20.

¹H NMR: δ=3.71 (s, 0.6H), 3.89 (s, 2.4H), 6.01 (d, J=8.8 Hz, 0.2H), 6.64 (d, J=7.7 Hz, 0.2H), 6.70 (d, J=8.8 Hz, 0.8H), 6.90 (s, 0.8H), 6.99 (d, J=8.0 Hz, 1H), 7.10 (d, J=7.7 Hz, 0.8H), 7.27-7.31 (m, 2H), 7.39-7.48 (m, 3.2H), 7.56-7.65 (m, 2H), 7.94 (s, 1H), 8.02 (d, J=7.7 Hz, 1H), 8.11 (d, J=7.7 Hz, 1H), 8.37 (s, 1H), 9.92 (s, 0.8H), 10.36 (s, 0.2H). ¹³C NMR: δ=56.0, 109.2, 114.2, 122.2, 124.2, 125.3, 125.7, 125.8, 128.3, 128.8, 129.1, 129.2, 129.7, 130.2, 130.9, 130.9, 131.0, 133.5, 134.1, 134.7, 134.8, 136.5, 137.4, 138.1, 139.5, 159.9, 188.2. Anal. Calcd. C₂₆H₁₉NO₃: C, 79.98; H, 4.72; N, 3.45. Found: C, 79.85; H, 4.92; N, 3.45.

1-(4'-Isoquinolyl)-8-(3'-formyl-4'-hydroxyphenyl)naphthalene N-oxide (2)

A solution of 7 (350 mg, 0.86 mmol) and BBr₃ (1M in CH₂Cl₂, 2.6 mL, 2.6 mmol) in 10 mL of CH₂Cl₂ was stirred at room temperature for 2 hours. The resulting mixture was quenched with 2-propanol, washed with water, dried over MgSO₄, and concentrated in vacuo. Purification by flash chromatography on silica gel (CH₂Cl₂:MeOH 20:1) afforded 253 mg (0.65 mmol, 75% yield) of a white solid. NMR analysis showed a mixture of syn and anti isomers with a ratio of 70:30.

¹H NMR: δ=5.96 (d, J=8.4 Hz, 0.3H), 6.59 (s, 1H), 6.69 (d, J=8.4 Hz, 0.7H), 7.06-7.17 (m, 2H), 7.27-7.48 (m, 2H), 7.66-7.87 (m, 5H), 7.89-7.92 (m, 1H), 8.04 (d, J=8.10 Hz, 1H), 8.12 (d, J=8.1 Hz, 1H), 8.34 (s, 0.3H), 8.44 (s, 0.7H), 9.08 (s, 0.7H), 9.82 (s, 0.3H), 10.60 (s, 0.7H), 10.98 (s, 0.3H). ¹³C NMR: δ=114.7, 115.2, 117.9, 124.9, 125.3, 125.6, 125.7, 126.0, 128.3, 128.7, 128.9, 129.0, 129.3, 129.3, 129.4, 129.4, 130.7, 130.8, 130.9, 131.0, 131.0, 132.9, 133.0, 134.2, 134.7, 134.9, 136.4, 136.8, 137.0, 137.8, 137.8, 139.2, 139.2, 159.2, 159.8, 195.2, 196.0. Anal. Calcd. C₂₆H₁₇NO₃: C, 79.78; H, 4.38; N, 3.58. Found: C, 79.81; H, 4.72; N, 3.40.

Synthesis of 1-(4'-Pyridyl)-8-(3'-formyl-4'-hydroxyphenyl)naphthalene N-oxide (3) and Characterization

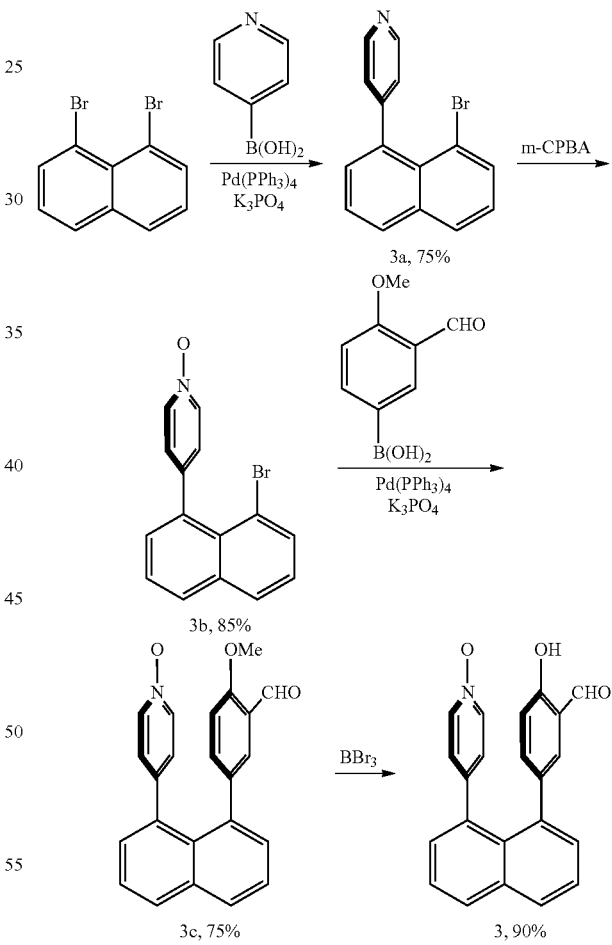

1-(4'-Pyridyl)-8-bromonaphthalene (3a)

A solution of 1,8-dibromonaphthalene (500 mg, 1.7 mmol), 4-pyridineboronic acid (322 mg, 2.6 mmol), Pd(PPh₃)₄ (151.5 mg, 0.13 mmol), and K₃PO₄ (927.7 mg, 4.4 mmol) in 18 mL of toluene:EtOH:water (3:2:1 v/v) was stirred at 90° C. for 6 hours. The resulting mixture was allowed to cool to room temperature, quenched with water, and extracted with CH₂Cl₂. The combined organic layers were dried over MgSO₄ and concentrated in vacuo. Purification by flash chromatography on silica gel (CH₂Cl₂: EtOAc 2:1) afforded 360 mg (1.3 mmol, 75% yield) of a yellow solid.

¹H NMR: δ=7.31-7.38 (m, 4H), 7.50 (dd, J=7.3, Hz, 8.0 Hz, 1H), 7.79 (d, J=6.6 Hz, 1H), 7.90 (dd, J=8.3 Hz, 8.3 Hz, 2H), 8.63 (d, J=5.7 Hz, 2H). ¹³C NMR: δ=119.6, 125.3, 125.4, 126.5, 129.0, 129.9, 131.0, 134.0, 136.0, 137.5, 148.6, 151.4. Anal. Calcd. C, 63.40; H, 3.55; N, 4.93. Found: C, 63.39; H, 3.52; N, 4.82.

1-(4'-Pyridyl)-8-bromonaphthalene N-oxide (3b)

A solution of 3a (400 mg, 1.4 mmol) and m-CPBA (729 mg, 4.2 mmol) in 10 mL of CH₂Cl₂ was stirred at room temperature for 8 hours. The mixture was washed with 2M NaOH, dried over MgSO₄, and concentrated in vacuo. Purification by flash chromatography on silica gel (CH₂Cl₂: EtOH 20:1) and recrystallization from CHCl₃ and hexanes (1:1 v/v) afforded 357 mg (1.2 mmol, 85% yield) of a light brown solid containing 33% of chloroform based on NMR analysis.

¹H NMR: δ=7.29 (d, J=6.3 Hz, 2H), 7.35-7.41 (m, 2H), 7.53 (dd, J=7.6 Hz, 7.7 Hz, 1H), 7.82 (d, J=7.3 Hz, 1H), 7.92-7.97 (m, 2H), 8.30 (d, J=6.3 Hz, 2H). ¹³C NMR: δ=119.2, 125.4, 126.8, 127.4, 128.9, 129.2, 130.5, 140.0, 134.2, 135.6, 136.1, 138.1, 142.4. Anal. Calcd. C₁₅H₁₀BrNO.(CHCl₃)₁/₃: C, 54.18; H, 3.06; N, 4.12. Found: C, 54.20; H, 3.44; N, 4.10.

1-(4'-Pyridyl)-8-(3'-formyl-4'-methoxyphenyl)naphthalene N-oxide (3c)

A solution of 3b (200 mg, 0.7 mmol), 3-formyl-4-methoxyphenylboronic add (180 mg, 1.0 mmol), Pd(PPh₃)₄ (58.0 mg 0.05 mmol), and K₃PO₄ (353.4 mg, 1.7 mmol) in 12 mL of toluene:EtOH:water (3:2:1 v/v) was stirred at 100° C. for 12 hours. The resulting mixture was allowed to cool to room temperature, quenched with water, and extracted with CH₂Cl₂. The combined organic layers were dried over MgSO₄ and concentrated in vacuo. Purification by flash chromatography on silica gel (CH₂Cl₂:EtOH 20:1) and recrystallization from CH₂Cl₂ and hexanes (1:1 v/v) afforded 186 mg (0.53 mmol, 75% yield) of a brown solid containing 33% of dichloromethane based on NMR analysis.

¹H NMR: δ=3.93 (s, 3H), 6.75-6.85 (m, 3H), 7.24 (m, 1H), 7.36 (d, J=7.9 Hz, 1H), 7.43-7.46 (m, 2H), 7.55-7.61 (m, 2H), 7.74-7.78 (m, 2H), 7.96 (dd, J=8.1 Hz, 8.2 Hz, 2H), 10.39 (s, 1H). ¹³C NMR: δ=56.2, 111.5, 123.7, 125.2, 125.8, 126.7, 128.7, 129.1, 129.6, 130.3, 130.6, 131.0, 135.0, 135.2, 135.4, 136.6, 137.4, 137.6, 141.5, 161.0, 189.3. Anal. Calcd. C₂₃H₁₇NO₃.(CH₂Cl₂)₁/₃: C, 73.04; H, 4.64; N, 3.65. Found: C, 73.10; H, 5.01; N, 3.60.

1-(4'-Pyridyl)-8-(3'-formyl-4'-hydroxyphenyl)naphthalene N-oxide (3)

A solution of 3c (200 mg, 0.6 mmol) and BBr₃ (1M in CH₂Cl₂ 1.7 ml, 1.7 mmol) in 10 mL of CH₂Cl₂ was stirred at room temperature for 2 hours. The resulting mixture was quenched with 2-propanol, washed with water, dried over MgSO₄, and concentrated in vacuo. Purification by flash chromatography on silica gel (CH₂Cl₂:EtOH 20:1) and recrystallization from CH₂Cl₂ and hexanes (1:1 v/v) afforded 184 mg (0.54 mmol, 90% yield) of a yellow solid containing 66% of dichloromethane based on NMR analysis.

¹H NMR: δ=6.78 (d, J=8.3 Hz, 1H), 6.91 (m, 2H), 7.21-7.26 (m, 2H), 7.40 (d, J=6.0 Hz. 1H), 7.46 (d, J=7.0 Hz, 1H), 7.58-7.65 (m, 2H), 7.87-7.95 (m, 2H), 8.00 (dd, J=7.1 Hz, 7.3 Hz, 2H), 9.78 (s, 1H), 10.84 (s, 1H). ¹³C NMR: δ=117.5, 119.7, 125.4, 126.0, 128.7, 129.2, 130.4, 131.0, 134.3, 134.5, 135.3, 135.6, 137.4, 138.0, 141.2, 160.6, 195.6, Anal. Calcd. C₂₂H₁₅NO₃.(CH₂Cl₂)₂/₃: C, 68.41; H, 4.14; N, 3.52. Found: C, 68.29; H, 4.17; N, 3.47.

2. Enantioselective Sensing Experiments

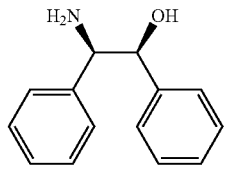

9

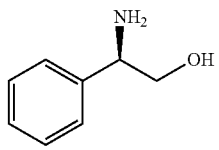

10

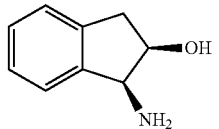

11

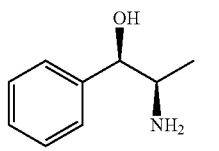

12

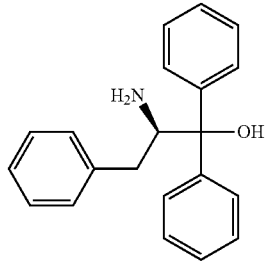

13

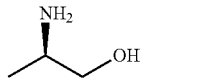

14

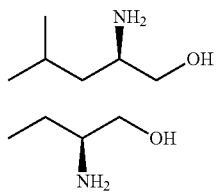

15

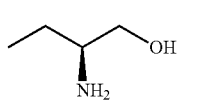

16

-continued

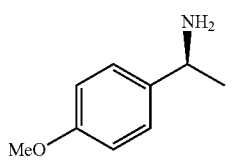
17

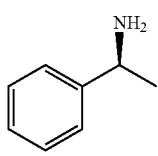
18

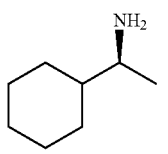
19

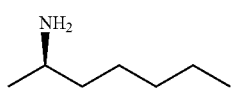
20

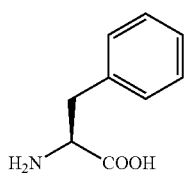
21

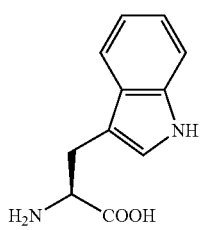
22

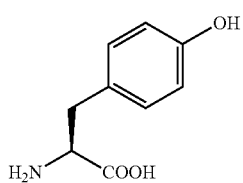
23

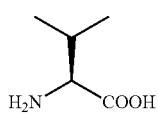
24

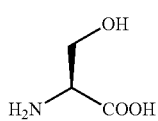
25

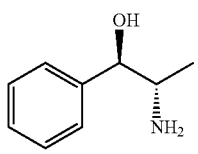
26

-continued

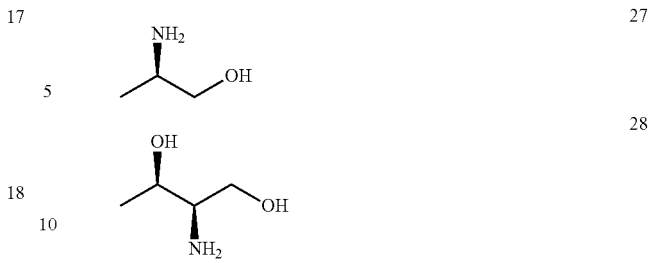

General Procedure for Chemosensing of Substrates 9-20

A stock solution of sensor 1 or 2 (0.00375 M) in CHCl$_3$ was prepared and portions of 350 µL were transferred to 4 mL vials. Solutions of the substrates (0.026 M in CHCl$_3$) were prepared. To each vial containing 350 µL of stock solution was added 1 equivalent (50 µL, 0.0013 mmol) of the substrate. The reactions were stirred overnight for sensor 1 and 15 minutes for sensor 2. The reaction times can be reduced to 5 hours for sensor 1 by addition of 10 mol % of trifluoroacetic acid or p-toluenesulfonic acid. The CD analysis was conducted with sample concentrations of $7.50 \times 10^{-5}$ M in MeOH for sensor 1 and in hexanes for sensor 2. CD spectra were collected with a standard sensitivity of 100 mdeg, a data pitch of 0.5 nm, a band width of 1 nm, a scanning speed of 500 nm s$^{-1}$ and a response of 0.5 s using a quartz cuvette (1 cm path length). The data were baseline corrected and smoothed using a binomial equation. Control experiments with free substrates showed no CD signal in the region of interest.

General Procedure for Chemosensing of Substrates 21-25

A stock solution of sensor 1, 2, or 3 (0.005 M) in DMSO was prepared and portions of 1 mL were transferred to 5 mL vials containing substrate 21-25 (0.005 mmol). Tetrabutylammonium hydroxide (1M in methanol, 0.005 mmol, 5 µL) was then added. The reactions were stirred overnight for sensor 1 and 15 minutes for sensors 2 and 3. CD analysis was conducted with sample concentrations of $7.50 \times 10^{-5}$ M in CHCl$_3$ for all sensors and the instrument settings were the same as for substrates 9-20.

Figure 20:
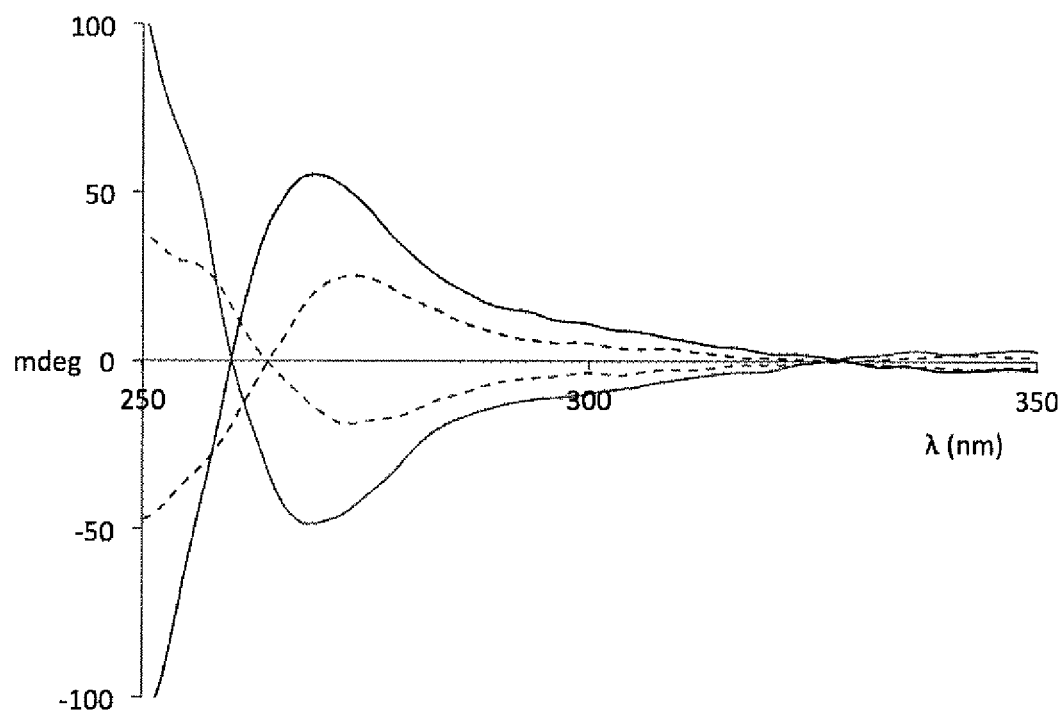
FIG. 20: CD Spectra of the imines obtained from 1 and (1R,2R)-9 in CHCl$_3$ (dashed) or MeOH (solid) and (1S,2S)-9 in CHCl$_3$ (dashed) or MeOH (solid).

The imines obtained with sensor 1 and amino alcohols or amines showed solvent-dependent CD readouts. For comparison purposes, the imines derived from 9, 10, and 18 were formed as described above and CD spectra were collected in CHCl$_3$ and methanol. CD Spectra of the imines obtained from 1 and (1R,2R)-9 in CHCl$_3$ (dashed) or MeOH (solid) and (1S,2S)-9 in CHCl$_3$ (dashed) or MeOH (solid) (FIG. 20).

Comparison of CD Output Obtained with the Protonated and Deprotonated Form of the Imine Obtained from Sensors 1, 2, and 3 and Amino Acids Imine formation with sensor 3 and amino acids 21, 22, 23, and 25 was conducted in the presence of TBAOH as described above. After the condensation was complete, 1 equivalent of HCl (1.25 M in EtOH, 4 µL) was added, changing the color from dark to light yellow. CD spectra were collected as described above.

Scheme 4: Condensation of 3 with amino acid 21 in the presence of TBAOH, followed by addition of 1 equivalent of HCl.

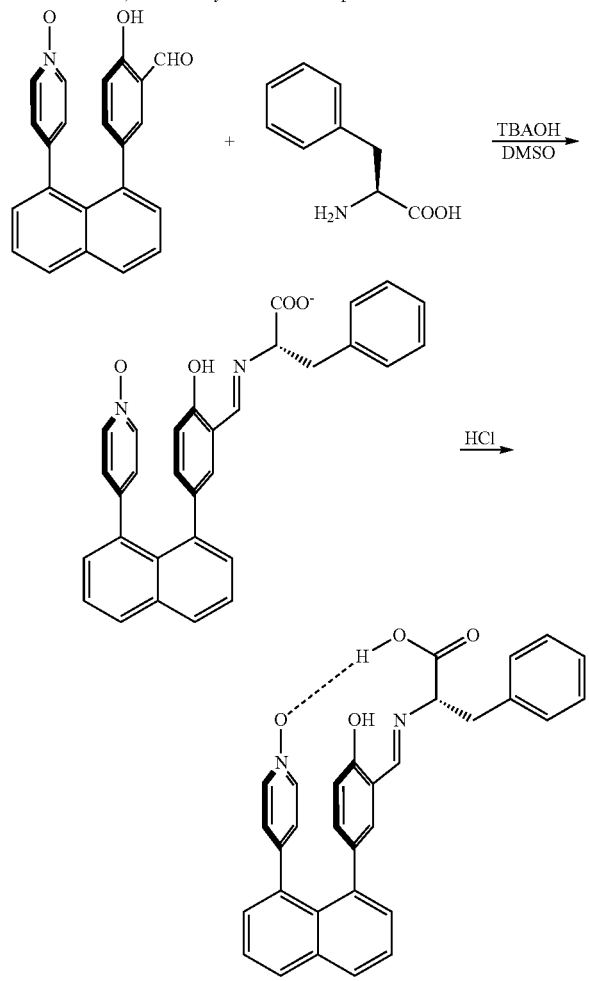

Figure 21:
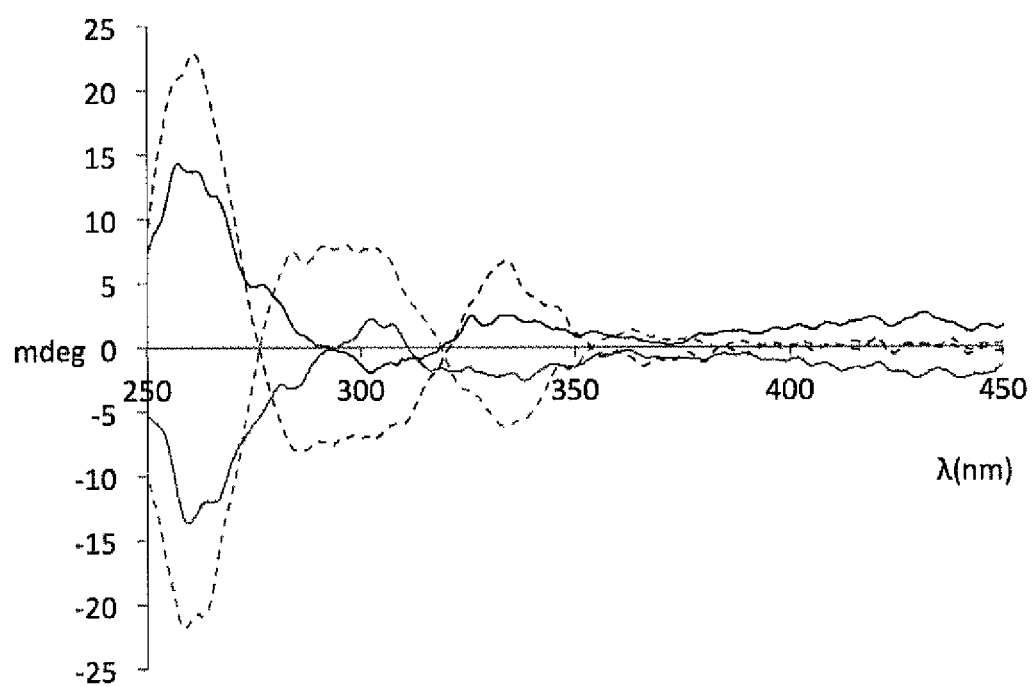
FIG. 21: CD Spectra of the imine obtained from 3, TBAOH and (R)-21 (solid) and (S)-21 (solid). CD response of the imine obtained from 3 and (R)-21 (dashed) and (S)-21 (dashed) upon addition of HCl.

For illustration, CD Spectra of the imine obtained from 3, TBAOH and (R)-21 (solid) and (S)-21 (solid). CD response of the imine obtained from 3 and (R)-21 (dashed) and (S)-21 (dashed) upon addition of HCl (FIG. 21).

Imine formation with sensor 2 and amino acid 22 was conducted in the presence of TBAOH as described above. After the condensation was complete, 1 equivalent of HCl (1.25 M in EtOH, 4 µL) was added and a CD spectrum was collected as described above.

Figure 22:
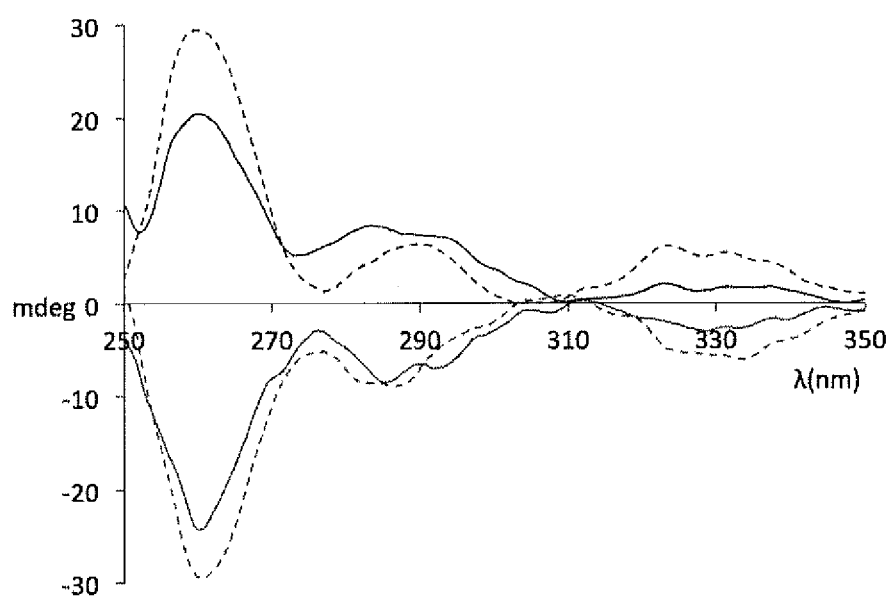
FIG. 22: CD Spectra of the imine obtained from 2, TBAOH and (R)-22 (solid) and (S)-22 (solid). CD response of the imine obtained from 2 and (R)-22 (dashed) and (S)-22 (dashed) upon addition of HCl.
Figure 23:
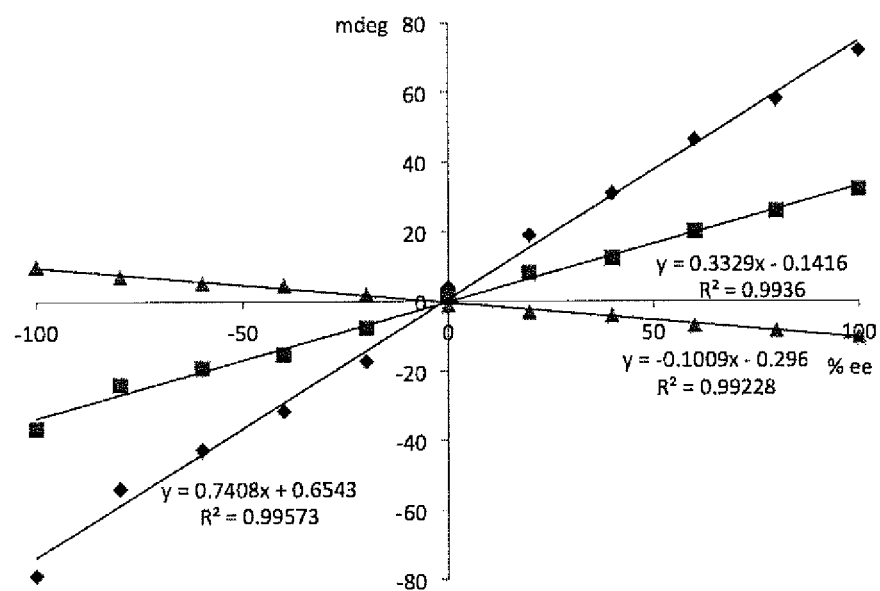
FIG. 23: Linear relationship between the CD amplitude at 260 nm (diamond) and 290 nm (triangle) nm and the enantiomeric excess of 23 with chemosensor 3.
Figure 24:
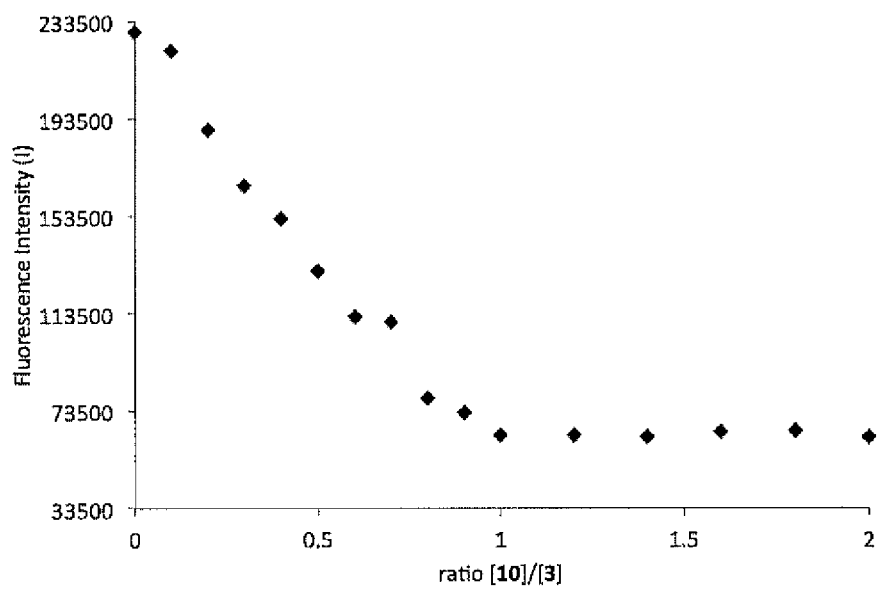
FIG. 24: Fluorescence intensity (I) measured at 450 nm plotted against equivalents of 23 with chemosensor 3.
Figure 25:
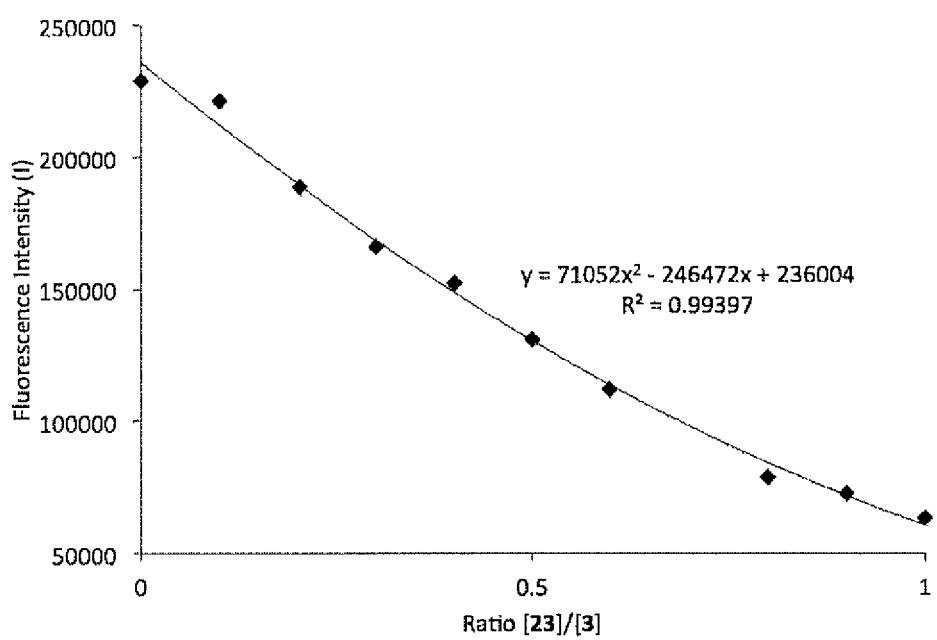
FIG. 25: Curve fitting of the fluorescence emission at 450 nm of 23 with chemosensor 3.

CD Spectra of the imine obtained from 2, TBAOH and (R)-22 (solid) and (S)-22 (solid). CD response of the imine obtained from 2 and (R)-22 (dashed) and (3)-22 (dashed) upon addition of HCl (FIG. 22).

General Procedure for Chemosensing of Substrates 9-11, 13-16, and 26-27

To test the general utility of 3 as enantioselective chemosensor, condensation reactions were performed with amino alcohols 9-11, 13-16, and 26-27 (only one enantiomer shown) and the chiroptical properties of the resulting imines were analyzed by CD spectroscopy.

As a specific example, solution of 3 (10 mg, 0.03 mmol) and 1.0 equivalent of amino alcohol (1S,2R)-9 was stirred under air. The solution changed immediately from colorless to yellow. The imine formation was evident from NMR analysis showing the disappearance of the formyl signal and electrospray mass spectrometry.

A stock solution of 3 (0.00375 M) in CHCl$_3$ was prepared and portions of 350 µL were transferred to 4 mL vials. Solutions of the substrates (0.1313 M in CHCl$_3$) were prepared. To each vial containing 350 µL stock solution was added 1 equivalent (10 µL) of the substrate. The colorless solutions changed immediately to a dark yellow. The reactions were stirred under air for 90 minutes. The CD analysis was conducted with sample concentrations of 7.50×10$^{-5}$ M in hexanes. CD spectra were collected with a standard sensitivity of 100 mdeg, a data pitch of 0.5 nm, a band width of 1 nm, a scanning speed of 500 nm s$^{-1}$ and a response of 0.5 s using a quartz cuvette (1 cm path length). The data were baseline corrected and smoothed using a binomial equation. Control experiments with 9-11, 13-16, and 26-27 showed that the free substrates are CD silent in the region of interest.

3. Quantitative Ee and Concentration Analysis

Determination of ee Using the Imine Obtained from 2 and Amino Alcohol 10

A calibration curve was constructed using samples of 10 with varying ee. Stock solutions of 2 (0.00375 M in CHCl$_3$) with varying enantiomeric composition (+100, +80, +60, +40, +20, 0, −20, −40, −60, −80, −100 ee) were prepared and the condensation reaction was carried out as described above. The CD amplitudes measured at 275, 295, and 325 nm were plotted against % ee.

Four scalemic samples of 10 were prepared and then treated with 2 as described above. Using the linear regression equations obtained from the calibration curves and the measured CD amplitudes at 275, 295, and 325 nm, the enantiomeric excess of the scalemic samples was determined with good accuracy.

Experimentally Determined Ee of Four Scalemic Samples of 10 Using the CD Maxima at 275, 295 and 325 nm

| Actual % ee (R) | Calculated % ee at 275 nm (R) | Calculated % ee at 295 nm (R) | Calculated % ee at 325 nm (R) | Average |
|---|---|---|---|---|
| 87.0 | 92.0 | 96.6 | 87.1 | 91.9 |
| 76.0 | 62.8 | 77.1 | 77.7 | 72.5 |
| −68.0 | −65.4 | −66.3 | −59.5 | −63.7 |
| −89.0 | −85.6 | −82.0 | −92.7 | −86.8 |

Determination of ee Using the Imine Obtained from 2 and Amino Acid 22

A calibration curve was constructed using samples of 22 with varying ee. Stock solutions of 2 (0.00375 M in DMSO) with varying enantiomeric composition (+100, +80, +60, +40, +20, 0, −20, −40, −60, −80, −100 ee) were prepared and the condensation reaction was carried out as described above for amino acids. A full equivalent of HCl (1.3 µL, 0.0013 mmol) was added to each vial and CD spectra were obtained as described above. The CD amplitudes measured at 260 and 290 nm were plotted against % ee.

Four scalemic samples of 22 were prepared and then treated with 2 as described above. Using the linear regression equations obtained from the calibration curves and the measured CD amplitudes at 260 and 290 nm, the enantiomeric excess of the scalemic samples was determined with good accuracy.

Experimentally Determined Ee of Four Scalemic Samples of 22 Using the CD Maxima at 260 and 290 nm

| Actual % ee (R) | Calculated % ee at 260 nm (R) | Calculated % ee at 290 nm (R) | Average |
|---|---|---|---|
| 87.0 | 84.1 | 86.4 | 85.3 |
| 12.0 | 10.8 | 10.6 | 10.7 |
| −68.0 | −67.8 | −67.7 | −67.8 |
| −89.0 | −90.4 | −89.4 | −89.9 |

Determination of the Concentration of 10 Using the Imine Obtained from 2

The change in the fluorescence of the sensor upon imine formation was analyzed, A calibration curve was constructed using samples containing various amounts of 10. First, 350 μL solutions of 2 (0.00375 M in CHCl$_3$) were placed in 16 vials. To each vial was then transferred a solution of 10 (0.065 M) in varying amounts (0, 10, 20, 30, 40, 50, 60, 70, 80, 90, 100, 110, and 120 mol %) and the condensation reaction was carried out as described above. Fluorescence spectra were collected using an excitation wavelength of 340 nm with slit widths of 3 nm and 6 nm and a quartz cuvette (1 cm path length). The fluorescence intensity at 515 nm increased as the concentration of 9 increased from 0 to 100 mol %. When the concentration of 10 was in excess of 100 mol %, the intensity remained constant. Plotting and curve fitting of the fluorescence intensity (I) at 515 nm against the concentration (c) of 10 ranging from 0 to 100 mol % gave a polynomial equation $(I=-762.79(c)^2+1773.5(c)+180.29)$ with $R^2=0.99415$.

Four solutions of sensor 2 were prepared and added to solutions of varying concentrations of 10 as described above. Using the regression equation obtained from the calibration curve and the measured fluorescence intensity at 515 nm, the concentration of these samples was determined with high accuracy.

Experimentally Determined Concentrations of Four Samples of Varying Concentration of 10 Using the Fluorescence Response at 515 nm

| Actual Concentration (mM) | Calculated Concentration (mM) |
|---|---|
| 0.63 | 0.63 |
| 1.34 | 1.30 |
| 2.67 | 2.62 |
| 3.23 | 3.38 |

Determination of ee Using the Imine Obtained from 3 and Amino Acid 23

A calibration curve was constructed using samples of 23 with varying ee. Stock solutions of 3 (0.00375 M in DMSO) with varying enantiomeric composition (+100, +80, +60, +40, +20, 0, −20, −40, −60, −80, −100 ee) were prepared and the condensation reaction was carried out as described above for amino acids. One equivalent of HCl (1.3 μL, 0.0013 mmol) was added to each vial and CD spectra were obtained as described above. The CD amplitudes measured at 274, 303, and 335 nm were plotted against % ee.

Experimentally Determined Ee of Four Scalemic Samples of 23 Using the CD Maxima at 274, 303 and 335 nm

| Actual % ee (R) | Calculated % ee at 274 nm (R) | Calculated % ee at 303 nm (R) | Calculated % ee at 335 nm (R) | Average |
|---|---|---|---|---|
| 87.0 | 87.4 | 88.3 | 90.1 | 88.6 |
| 76.0 | 74.2 | 73.8 | 76.7 | 74.9 |
| 12.0 | 11.8 | 13.2 | 12.9 | 12.6 |
| −26.0 | −27.1 | −28.3 | −25.3 | −26.9 |
| −68.0 | −66.3 | −65.4 | −66.8 | −66.2 |

Determination of the Concentration of 23 Using the Imine Obtained from 3

The change in the fluorescence of the sensor upon imine formation was analyzed. A calibration curve was constructed using samples containing various amounts of 23. First, 350 solutions of 3 (0.00375 M in DMSO) were placed in 16 vials. To each vial was then transferred a solution of 23 (0.065 M in DMSO) in varying amounts (0, 10, 20, 30, 40, 50, 60, 70, 80, 90, 100, 110, 120, 140, 160, 180, and 200 mol %) and the condensation reaction was carried out as described above for amino acids. Fluorescence spectra were collected using an excitation wavelength of 350 nm with slit widths of 3 nm and 6 nm and a quartz cuvette (1 cm path length). The fluorescence intensity at 450 nm decreased as the concentration of 23 increased from 0 to 100 mol %. When the concentration of 23 was in excess of 100 mol %, the intensity remained constant. Plotting and curve fitting of the fluorescence intensity (I) at 450 nm against the concentration (c) of 23 ranging from 0 to 100 mol % gave a polynomial equation $(I=71052 (c)^2-246472(c)+236004)$ with $R^2=0.99397$.

Five solutions of sensor 3 were prepared and added to solutions of varying concentrations of 23 as described above. Using the regression equation obtained from the calibration curve and the measured fluorescence intensity at 450 nm, the concentration of these samples was determined with high accuracy.

Experimentally Determined Concentrations of Five Samples of Varying Concentration of 23 Using the Fluorescence Response at 450 nm

| Actual Concentration (mM) | Calculated Concentration (mM) |
|---|---|
| 0.56 | 0.59 |
| 1.01 | 1.08 |
| 1.73 | 1.73 |
| 2.36 | 2.32 |
| 2.93 | 2.97 |

Determination of ee Using the Imine Obtained from 3 and Amino Alcohol 9

A calibration curve was constructed using samples of 9 with varying ee. Stock solutions of 9 with varying ee composition (+100.0, +80.0, +60.0, +40.0, +20.0, 0.0, −20.0, −40.0, −60.0, −80.0, −100.0) were added to 0.00375 M solutions of 3 and the condensation reaction and CD analysis were carried out as described above. The Cotton effect amplitudes measured at 260 nm were plotted against % ee.

Five scalemic samples of 9 were prepared and then treated with sensor 3 as described above. Using the linear regression equation obtained from the calibration curve and the measured Cotton effect amplitude at 260 nm, the enantiomeric excess of these samples was determined. Experimentally obtained data were within 1.8% of the actual values.

Experimentally Determined Ee of Five Scalemic Samples of 9 Using the CD Maximum at 260 nm

| Actual % ee (1R,2S) | Calculated % ee (1R,2S) |
|---|---|
| 87.0 | 85.6 |
| 76.0 | 77.8 |
| −26.0 | −26.4 |
| −68.0 | −67.0 |
| −89.0 | −90.3 |

Calibration curves were also generated using the CD amplitudes at 290 nm and 340 nm. Using the linear regression equations obtained from the calibration curves and the measured amplitudes at 290 nm and 340 nm, the enantiomeric excess of the scalemic samples was determined with good accuracy.

Experimentally Determined Ee of Five Scalemic Samples of 9 Using the CD Maxima at 260, 290 and 340 nm

| Actual % ee (1R,2S) | Calculated % ee at 260 nm (1R,2S) | Calculated % ee at 290 nm (1R,2S) | Calculated % ee at 340 nm (1R,2S) |
|---|---|---|---|
| 87.0 | 85.6 | 85.7 | 84.4 |
| 76.0 | 77.8 | 77.7 | 74.7 |
| −26.0 | −26.4 | −30.2 | −29.8 |
| −68.0 | −67.0 | −69.1 | −67.1 |
| −89.0 | −90.3 | −87.0 | −90.2 |

Determination of ee Using the Imine Obtained from 3 and Amino Alcohol 16

A calibration curve was constructed using samples prepared by the reaction of chemosensor 3 and 16 with varying ee, as described above. The CD amplitudes observed at 275 nm were plotted against the enantiomeric excess of the amino alcohol used.

Four scalemic samples of 16 were prepared and then treated with sensor 3 as described above, and the ee was calculated using the linear regression equation with good accuracy.

Experimentally Determined Ee of Five Scalemic Samples of 16 Using the CD Maximum at 275 nm

| Actual % ee (R) | Calculated % ee (R) |
|---|---|
| 87.0 | 86.8 |
| 76.0 | 71.3 |
| −68.0 | −64.6 |
| −89.0 | −83.1 |

Calibration curves were also generated using the CD amplitudes at 257 nm and 340 nm. Using the linear regression equations obtained from the respective calibration curves and the measured amplitudes at 257 nm and 340 nm, the enantiomeric excess of the scalemic samples was determined.

Experimentally Determined Ee of Five Scalemic Samples of 16 Using the CD Maxima at 257, 275 and 340 nm

| Actual % ee (1R,2S) | Calculated % ee at 257 nm (1R,2S) | Calculated % ee at 275 nm (1R,2S) | Calculated % ee at 340 nm (1R,2S) |
|---|---|---|---|
| 87.0 | 82.7 | 86.8 | 76.6 |
| 76.0 | 71.2 | 71.3 | 70.4 |
| −68.0 | −60.8 | −64.6 | −71.1 |
| −89.0 | −79.9 | −83.1 | −85.3 |

Determination of the Concentration of 9 Using Chemosensor 3

The change in the fluorescence of the sensor upon imine formation was analyzed. A calibration curve was constructed using samples containing various amounts of 9. First, 350 ul solutions of 3 (0.00375 M in $CHCl_3$) were added to 16 vials. To each vial was then transferred a solution of 9 (0.13 M, 10 μl) in varying amounts (0, 10, 20, 30, 40, 50, 60, 70, 80, 90, 100, 120, 140, 160, 180 and 200 mol %) and the condensation reaction was carried out as described above. Fluorescence spectra were collected using an excitation wavelength of 340 nm with slit widths of 3 nm and 6 nm and a quartz cuvette (1 cm path length). The fluorescence intensity at 515 nm increased as the concentration of 9 increased from 0 to 100 mol %, followed by quenching in the presence of excess of 5. Plotting and curve fitting of the fluorescence intensity (I) at 515 nm against the concentration (c) of 9 ranging from 0 to 100 mol % gave a polynomial equation (I=−993.63 $(c)^2$+2406.8(c)+127.41) with $R^2$=0.99511.

Five solutions of sensor 3 were prepared and added to solutions of varying concentrations of 9 as described above. Using the regression equation obtained from the calibration curve and the measured fluorescence intensity at 515 nm, the concentration of these samples was determined. Experimentally obtained data were within 2.5% of the actual values.

Experimentally Determined Concentrations of Five Samples of Varying Concentration of 9 Using the Fluorescence Response at 515 nm

| Actual Concentration (mM) | Calculated Concentration (mM) |
|---|---|
| 0.56 | 0.57 |
| 1.01 | 0.99 |
| 1.73 | 1.63 |
| 2.39 | 2.39 |
| 2.93 | 2.94 |

Determination of the Concentration of 16

A calibration curve was constructed with samples of 16 using the same procedure as described above. The fluorescence intensity at 430 nm increased as the concentration of 16 increased from 0 to 100 mol %, followed by quenching in the presence of excess of 16. Plotting and curve fitting of the fluorescence intensity (I) at 430 nm against the concentration (c) of 16 up to 100 mol % gave a polynomial curve (I=−344127$(c)^2$+822310(c)+485183) with $R^2$=0.99678.

Five solutions of sensor 3 were prepared and added to solutions of varying concentrations of 16 as described above. Using the regression equation obtained from the calibration curve and the measured fluorescence intensity at 430 nm, the concentration of these samples was determined. Experimentally obtained data were within 5.4% of the actual values.

Experimentally Determined Concentrations of Five Samples of Varying Concentration of 16 Using the Fluorescence Response at 430 nm

| Actual Concentration (mM) | Calculated Concentration (mM) |
|---|---|
| 0.56 | 0.71 |
| 1.01 | 0.95 |
| 1.73 | 1.65 |
| 2.93 | 2.57 |

Linearity of the CD Response Versus the Concentration of the Imine Formed

Chemosensor 3 (0.00375M in $CHCl_3$), was treated with various amounts of 9 (100% ee) and the CD response of the imine formed was measured as described above. Plotting the CD amplitudes at 260 nm of the corresponding imine against the amount of 9 showed a linear response.

Simultaneous Ee and Concentration Determination

For simultaneous determination of both concentration and ee, solutions of 3 were treated with samples containing scalemic 9 at various concentrations. First, a fluorescence spectrum was obtained via the method described above, and the concentration was calculated using the regression equation obtained in section 4.3. Then, a CD spectrum was obtained as described above. The Cotton effect intensity (mdeg) was normalized (the CD effect increases linearly with the concentration of 9, see section 4.5.) for the concentration calculated by the fluorescence analysis using the relative mol % ($\chi$) of 9 as shown in equation 1. This value was then applied in the linear regression equation obtained in section 4.1. to determine the enantiomeric excess (Equation 1).

$$ee = \frac{\frac{mdeg}{\chi} + 1.0596}{-0.7486} \qquad \text{Equation 1}$$

Actual and Calculated % Ee, Total Concentration and Absolute Configuration of Four Scalemic Samples of 9 Determined by the Combined Fluorescence and CD Responses of Chemosensor 1

| Actual Concentration (mM) | Actual % ee | Abs. Config. (Major Enantiomer) | Calculated Concentration (mM) | Calculated % ee | Abs. Config. (Major Enantiomer) |
|---|---|---|---|---|---|
| 1.20 | 28.0 | 1S,2R | 1.21 | 24.8 | 1S,2R |
| 2.14 | 10.0 | 1S,2R | 1.97 | 13.7 | 1S,2R |
| 2.70 | 52.0 | 1R,2S | 2.65 | 52.9 | 1R,2S |
| 3.04 | 64.0 | 1R,2S | 3.00 | 62.4 | 1R,2S |

TABLE 1

Summary of the CD sensing results with chemosensors 1, 2 and 3.

| Entry | Sensor | Substrate Class | Substrate | $\Delta^a$ (mdeg) | Predicted CD Signal[b] |
|---|---|---|---|---|---|
| 1 | 1 | AA | (1S,2R)-9 | −49 | − |
|  | 1 | AA | (1R,2S)-9 | +55 | + |
| 2 | 1 | AA | (R)-10 | −48 | − |
|  | 1 | AA | (S)-10 | +48 | + |
| 3 | 1 | AA | (1R,2R)-11 | −7 | − |
|  | 1 | AA | (1S,2S)-11 | +7 | + |
| 4 | 1 | AA | (1S,2R)-12 | −9 | − |
|  | 1 | AA | (1R,2S)-12 | +12 | + |
| 5 | 1 | MA | (R)-17 | −12 | − |
|  | 1 | MA | (S)-17 | +11 | + |
| 6 | 1 | MA | (R)-18 | −15 | − |
|  | 1 | MA | (S)-18 | +15 | + |
| 7 | 1 | MA | (R)-19 | −9 | − |
|  | 1 | MA | (S)-19 | +10 | + |
| 8 | 1 | MA | (R)-20 | −5 | − |
|  | 1 | MA | (S)-20 | +6 | + |
| 9 | 1 | AC | (R)-21 | −19 | − |
|  | 1 | AC | (S)-21 | +20 | + |
| 10 | 1 | AC | (R)-22 | −10 | − |
|  | 1 | AC | (S)-22 | +11 | + |
| 11 | 1 | AC | (R)-23 | −24 | − |
|  | 1 | AC | (S)-23 | +24 | + |
| 12 | 1 | AC | (R)-24 | −10 | − |
|  | 1 | AC | (S)-24 | +12 | + |
| 13 | 2 | AA | (1S,2R)-9 | +13 | + |
|  | 2 | AA | (1R,2S)-9 | −13 | − |
| 14 | 2 | AA | (R)-10 | +13 | + |
|  | 2 | AA | (S)-10 | −9 | − |
| 15 | 2 | AA | (1R,2R)-11 | +8 | + |
|  | 2 | AA | (1S,2S)-11 | −8 | − |
| 16 | 2 | AA | (1S,2R)-12 | +3 | + |
|  | 2 | AA | (1R,2S)-12 | −3 | − |
| 17 | 2 | AA | (R)-13 | +19 | + |
|  | 2 | AA | (S)-13 | −19 | − |
| 18 | 2 | AA | (R)-14 | +12 | + |
|  | 2 | AA | (S)-14 | −14 | − |
| 19 | 2 | AA | (R)-15 | +13 | + |
|  | 2 | AA | (S)-15 | −13 | − |
| 20 | 2 | AA | (R)-16 | +16 | + |
|  | 2 | AA | (S)-16 | −15 | − |
| 21 | 2 | AC | (R)-21 | +19 | + |
|  | 2 | AC | (S)-21 | −15 | − |
| 22 | 2 | AC | (R)-22 | +21 | + |
|  | 2 | AC | (S)-22 | −27 | − |
| 23 | 2 | AC | (R)-23 | +19 | + |
|  | 2 | AC | (S)-23 | −16 | − |
| 24 | 2 | AC | (R)-24 | +8 | + |
|  | 2 | AC | (S)-24 | −11 | − |
| 25 | 3[c] | AA | (1S,2R)-9 | +29 | + |
|  | 3[c] | AA | (1R,2S)-9 | −33 | − |
| 26 | 3[c] | AA | (R)-10 | +77 | + |
|  | 3[c] | AA | (S)-10 | −78 | − |
| 27 | 3[c] | AA | (1R,2R)-11 | +27 | + |
|  | 3[c] | AA | (1S,2S)-11 | −27 | − |
| 28 | 3[c] | AA | (1S,2R)-12 | +61 | + |
|  | 3[c] | AA | (1R,2S)-12 | −63 | − |
| 29 | 3[c] | AA | (R)-13 | +18 | + |
|  | 3[c] | AA | (S)-13 | −17 | − |
| 30 | 3[c] | AA | (R)-14 | +57 | + |
|  | 3[c] | AA | (S)-14 | −47 | − |
| 31 | 3[c] | AA | (R)-15 | +55 | + |
|  | 3[c] | AA | (S)-15 | −53 | − |
| 32 | 3[c] | AA | (R)-16 | +63 | + |
|  | 3[c] | AA | (S)-16 | −66 | − |
| 33 | 3[c] | AA | (1R,2R)-26 | +20 | + |
|  | 3[c] | AA | (1S,2S)-26 | −21 | − |
| 34 | 3 | AC | (R)-21 | +22 | + |
|  | 3 | AC | (S)-21 | −22 | − |
| 35 | 3 | AC | (R)-22 | +36 | + |
|  | 3 | AC | (S)-22 | −42 | − |
| 36 | 3 | AC | (R)-23 | +51 | + |
|  | 3 | AC | (S)-23 | −42 | − |

TABLE 1-continued

Summary of the CD sensing results with chemosensors 1, 2 and 3.

| Entry | Sensor | Substrate Class | Substrate | Δ[a] (mdeg) | Predicted CD Signal[b] |
|---|---|---|---|---|---|
| 37 | 3 | AC | (R)-25 | +22 | + |
|  | 3 | AC | (S)-25 | −22 | − |

[a]CD output at 270 nm for sensor 1 and 260 nm for sensors 2 and 3. The CD response to 25 was measured at 280 nm.
[b]Predicted CD sign at 270 nm for sensor 1, where R is negative and S is positive. Analysis of the CD readout at 260 nm for sensors 2 and 3 shows R enantiomers give a positive sign and S substrates give a negative CD response for all substrates.
MA = monoamine, AA = amino alcohol, AC = amino acid.

4. Spectroscopic and Spectrometric Analysis of the Imine Formation

Sensor 1 (20 mg, 0.047 mmol) was dissolved in 2 mL of $CDCl_3$ for real-time IR analysis. IR spectra of the stirred solution of 1 were collected for 5 minutes. Then, 10 (6.5 mg, 0.047 mmol) and p-toluenesulfonic acid (1M in EtOH, 4.7 µL, 0.0047 mmol) were added and the mixture was stirred for 2 hours. IR spectra were collected with 16 scans at 30-second intervals.

After addition of 10, the intensity of the aldehyde stretching at 1668 $cm^{-1}$ started to disappear and the imine stretching at 1635 $cm^{-1}$ steadily increased. After 5 hours, NMR and MS spectra were collected. ESI-MS data were collected by dissolving the imine in a 1:1 $CHCl_3$:MeOH mixture at a concentration of 1 mg/mL The NMR and MS measurements showed quantitative imine formation after 5 hours. MS analysis of the product identified the expected imine, and the characteristic NMR signal of the formyl proton in 1 (10.42 ppm) had disappeared.

Sensor 2 (20 mg, 0.049 mmol) was dissolved in 2 mL of $CDCl_3$ for real-time IR analysis. IR spectra of the stirred solution were collected for 5 minutes. Then, 10 (6.8 mg, 0.049 mmol) was added and the mixture was stirred for 1 hour. IR spectra were collected with 16 scans at 30-second intervals. After addition of 10, the intensity of the aldehyde stretching at 1680 $cm^{-1}$ started to disappear and the imine stretching at 1640 $cm^{-1}$ steadily increased. After 15 minutes, NMR and MS spectra were collected. The IR, NMR, and MS measurements showed quantitative imine formation after 15 minutes. MS analysis of the product identified the expected imine, and the characteristic NMR signal of the formyl proton in 2 (10.60 ppm) had disappeared.

Sensor 3 (20 mg, 0.059 mmol) was dissolved in 2 mL of $CDCl_3$ for real-time IR analysis. IR spectra of the stirred solution were collected for 5 minutes. Then, 10 (8.1 mg, 0.059 mmol) was added and the mixture was stirred for 30 minutes. IR spectra were collected with 16 scans at 30-second intervals. After addition of 10, the intensity of the aldehyde stretching at 1685 $cm^{-1}$ started to disappear and the imine stretching at 1645 $cm^{-1}$ steadily increased, After 15 minutes, NMR and MS spectra were collected. The IR, NMR, and MS measurements showed quantitative imine formation after 15 minutes. MS analysis of the product identified the expected imine, and the characteristic NMR signal of the formyl proton in 3 (10.84 ppm) had disappeared.

5. Crystallography

A single crystal of the imine formed from 2 and (1S,2R)-9 was obtained by slow diffusion of hexanes into a concentrated chloroform solution. Crystallographic analysis was performed at 100 K using a Siemens platform diffractometer with graphite monochromated Mo-Kα radiation (λ=0.71073 Å). Data were integrated and corrected using the Apex 2 program. The structure was solved by direct methods and refined with full-matrix least-square analysis using SHELX-97-2 software. Non-hydrogen atoms were refined with anisotropic displacement parameters. The asymmetric unit contains one imine molecule having (1S,2R,M,M) configuration and one chloroform molecule. Crystal structure data: Formula $C_{40}H_{30}N_2O_3$, M=586.23, crystal dimensions 0.5×0.3×0.1 mm, orthorhombic, space group $P2_12_12_1$, a=12.362(3) Å, b=14.611(3) Å, c=19.273(4) Å, α=90.0°, β=90.0°, γ=90.0°, V=3481.0 Å$^3$, Z=4, $\varrho_{calcd}$ =1.347 g cm$^{-3}$.

Important Crystallographic Distances [Å] and Angles [°] of the Imine Formed from 2 and (1S,3R)-9

| | |
|---|---|
| N1—H1 | 1.773 |
| Phenyl-Isoquinolyl (centroid to centroid) [Å] | 3.455 |
| Splaying Angle [°] | 10.1 |
| Twisting Angle [°] | 25.7 |

A single crystal of the imine formed from 3 and (1S,2R)-9 was obtained by slow diffusion of hexanes into a concentrated chloroform solution of the imine. Single crystal X-ray analysis was performed at 100 K using a Siemens platform diffractometer with graphite monochromated Mo-Kα radiation (λ=0.71073 Å). Data were integrated and corrected using the Apex 2 program. The structures were solved by direct methods and refined with full-matrix least-square analysis using SHELX-97-2 software. Non-hydrogen atoms were refined with anisotropic displacement parameters. The asymmetric unit contains four unique imine molecules with (1S,2R,M) configuration and three chloroform molecules. The imines A, C, and D show intramolecular hydrogen bonding between the alcohol moiety of 9 and the N-oxide group of the sensor. Crystal structure data: Formula $C_{36}H_{28}N_2O_3$, M=536.63, crystal dimensions 0.6×0.2×0.1 mm, monoclinic, space group $P2_1$, a=14.036(1) Å, b=9.731(5) Å, c=44.837(1) Å, α=90.0°, β=96.093°, γ=90.0°, V=6089.81 Å$^3$, Z=8, $\varrho_{calcd}$ =1.3668 g cm$^{-3}$.

Important Crystallographic Distances and Angles Imine Formed from 3 and (1S,2R)-9

| | A | B | C | D |
|---|---|---|---|---|
| O1—H3 [Å] | 1.573 | — | 1.593 | 1.946 |
| N2—H2 [Å] | 1.909 | 1.858 | 1.890 | 1.774 |
| Phenyl - Phenyl (centroid to centroid) [Å] | 3.338 | 3.765 | 3.425 | 3.391 |
| Splaying Angle [°] | 20.6 | 19.9 | 19.6 | 20.2 |
| Twisting Angle [°] | 4.8 | 44.2 | 8.2 | 3.1 |

[1]Gawley, R. E. Aubé, J. (ed.) Principles of Asymmetric Synthesis, In: Tetrahedron Organic Chemistry Series, Elsevier, New York, 1996.
[2]Leung, D.; Kang, S. O.; Anslyn, E. V. Chem. Soc. Rev. 2012, 41, 448-479.
[3]Selected examples of UV sensing of chiral compounds: (a) Zhu, L.; Anslyn, E. V. J. Am. Chem. Soc. 2004, 126, 3676-3677. (b) Leung, D.; Folmer-Andersen, J. F.; Lynch, V. M.; Anslyn, E. V. *J. Am. Chem. Soc.* 2008, 130, 12318-12327. (c) Leung, D.; Anslyn, E. V. *J. Am. Chem. Soc.* 2008, 130, 12328-12333. (d) Iwaniuk, D. P.; Yearick-Spangler, K.; Wolf, C. V. *J. Org. Chem.* 2012, 77, 5203-5208.

[4] Selected examples of enantioselective fluorescence sensing: (a) Lee, S. J.; Lin, W. *J. Am. Chem. Soc.* 2002, 124, 4554-4555. (b) Lin, J.; Hu, Q.-S.; Xu, M.-H.; Pu, L. *J. Am. Chem. Soc.* 2002, 124, 2088-2089. (c) Mei, X.; Wolf, C. *Chem. Commun.* 2004, 2078-2079. (d) Zhao, J.; Fyles, T. M.; James, T.; D. *Angew. Chem., Int. Ed* 2004, 43, 3461-3464. (e) Mei, X.; Wolf, C. *J. Am. Chem. Soc.* 2004, 126, 14736-14737. (f) Li, Z.-B.; Lin, J.; Pu, L. *Angew. Chem., Int. Ed.* 2005, 44, 1690-1693. (g) Tumambac, G. E.; Wolf, C. *Org. Lett.* 2005, 7, 4045-4048. (h) Mei, X.; Martin, R. M.; Wolf, C. *J. Org. Chem.* 2006, 71, 2854-2861. (i) Mei, X.; Wolf, C. *Tetrahedron Lett.* 2006, 47, 7901-7904. (j) Wu, Y.; Guo, H.; James, T. D.; Zhao, J. *J. Org. Chem.* 2011, 76, 5685-5695. (k) Wu, Y.; Guo, H.; Zhang, X.; James, T. D.; Zhao, *J. Chem. Eur. J.* 2011, 17, 7632-7644. (l) Yang, X.; Liu, X.; Shen, K.; Zhu, C.; Cheng, Y. *Org. Lett.* 2011, 13, 3510-3513. (m) He, X.; Zhang, Q.; Liu, X.; Lin, L. Feng, X. *Chem. Commun.* 2011, 47, 11641-11643. (n) Wanderley, M. M.; Wang, C.; Wu, C.-D.; Lin, W. *J. Am. Chem. Soc.* 2012, 134, 9050-9053. For a review: Pu, L. *Chem. Rev.* 2004, 104, 1687-1716.

[5] Selected examples of enantioselective CD sensing: (a) Superchi, S.; Casarini, D.; Laurita, A.; Bavoso, A.; Rosini, C. *Angew. Chem., Int. Ed* 2001, 40, 451-454. (b) Kurtan, T.; Nesnas, N.; Koehn, F. E.; Li, Y.-Q.; Nakanishi, K.; Berova, N. *J. Am. Chem. Soc.* 2001, 123, 5974-5982. (c) Huang, X.; Fujioka, N.; Pescitelli, G.; Koehn, F. E.; Williamson, R. T.; Nakanishi, K.; Berova, N. *J. Am. Chem. Soc.* 2002, 124, 10320-10335. (d) Mazaleyrat, J.-P.; Wright, K.; Gaucher, A.; Toulemonde, N.; Wakselman, M.; Oancea, S.; Peggion, C.; Formaggio, F.; Setnicka, V.; Keiderling, T. A.; Toniolo, C. *J. Am. Chem. Soc.* 2004, 126, 12874-12879. (e) Superchi, S.; Bisaccia, R.; Casarini, D.; Laurita, A.; Rosini, C. *J. Am. Chem. Soc.* 2006, 128, 6893-6902. (f) Holmes, A. E.; Das, D.; Canary, J. W. *J. Am. Chem. Soc.* 2007, 129, 1506-1507. (g) Dutot, L.; Wright, K.; Gaucher, A.; Wakselman, M.; Mazaleyrat, J.-P.; De Zotti, M.; Peggion, C.; Formaggio, F.; Toniolo, C. *J. Am. Chem. Soc.* 2008, 130, 5986-5992. (h) Sciebura, J.; Skowronek, P.; Gawronski, J. *Angew. Chem., Int. Ed.* 2009, 48, 7069-7072. (i) Sciebura, J.; Gawronski, J. *Chem. Eur. J.* 2011, 17, 13138-13141. (j) Kim, H.; So, S. M.; Yen, C. P.-H.; Vinhato, E.; Lough, A. J.; Hong, J.-I.; Kim, H.-J.; Chin, J. *Angew. Chem., Int, Ed* 2008, 47, 8657-8660. (k) Waki, M.; Abe, H.; Inouye, M. *Angew. Chem., Int. Ed.* 2007, 46, 3059-3061. (l) Katoono, R.; Kawai, H.; Fujiwara, K.; Suzuki, T. *J. Am. Chem. Soc.* 2009, 131, 16896-16904. Ghosn, M. W.; Wolf, C. *J. Am. Chem. Soc.* 2009, 131, 16360-16361. (m) Ghosn, M. W.; Wolf, C. *Tetrahedron* 2010, 66, 3989-3994. (n) Ghosn, M. W.; Wolf, C. *J. Org. Chem.* 2011, 76, 3888-3897. (o) Ghosn, M. W.; Wolf, C. *Tetrahedron* 2011, 67, 6799-6803. (p) Joyce, L. A.; Maynor, M. S.; Dragna, J. M.; da Cruz, G. M.; Lynch, V. M.; Canary, J. W.; Anslyn, E. V. *J. Am. Chem. Soc.* 2011, 133, 13746-13752. (q) You, L.; Pescitelli, G.; Anslyn, E. V.; Di Bari, L. *J. Am. Chem. Soc.* 2012, 134, 7117-7125. (r) Wezenberg, S. J.; Salassa, G.; Escudero-Adan, E. C.; Benet-Buchholz, J.; Kleij, A. W. *Angew. Chem., Int. Ed.* 2011, 50, 713-716. (s) Iwaniuk, D. P.; Wolf, C. *J. Am. Chem. Soc.* 2011, 133, 2414-2417. (t) Iwaniuk, D. P.; Wolf, C. *Org. Lett.* 2011, 13, 2602-2605. (u) Iwaniuk, D. P.; Bentley, K. W.; Wolf, C. *Chirality* 2012, 24, 584-589. Li, X.; Burrell, C. E.; Staples, R. J.; Borhan, B. *J. Am. Chem. Soc.* 2012, 134, 9026-9029. (v) Iwaniuk, D. P.; Wolf, C. *Chem. Commun.* 2012, 48, 11226-11228.

[6](a) Mei, X.; Wolf, C. *J. Am. Chem. Soc.* 2006, 128, 13326-13327, (b) Wolf, C.; Liu, S.; Reinhardt, B. C. *Chem. Commun,* 2006, 4242-4244. (c) Zhu, L.; Shabbir, S. H.; Anslyn, E. V. *Chem. Eur. J.* 2007, 13, 99-104. (d) Liu, S.; Pestano, J. P. C.; Wolf, C. *J. Org. Chem.* 2008, 73, 4267-4270. (e) Yu, S.; Pu, L. *J. Am. Chem. Soc.* 2010, 132, 17698-17700.

[7] Wolf, C. (ed.) Dynamic Stereochemistry of Chiral Compounds, RSC Publishing, Cambridge, UK, 2008, 84-94.

[8] Attempts to reverse the coupling sequence and to install the anthracene unit prior to the salicylaldehyde moiety were unsuccessful due to prevailing debromination.

[9] Bernard, A.; Ghiani, R.; Piras, P.; Rivoldini, A. *Synthesis* 1989, 287.

The invention claimed is:

1. A chemosensor compound of formula (I):

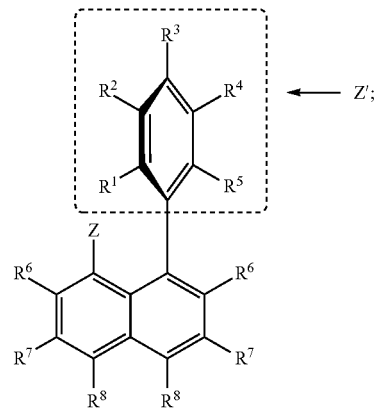

wherein $R^1$ and $R^5$ are independently hydrogen, halo, cyano, ($C_1$-$C_3$) alkyl, ($C_2$-$C_3$) alkenyl, or ($C_2$-$C_3$) alkynyl;

$R^2$ and $R^4$ are independently hydrogen, —$CO_2R^9$, —C(O)N($R^9$)$_2$, —$NR^9$—(C=$NR^9$)N($R^9$)$_2$, —$NR^9$—(C=O)OR$^9$, —O—(C=O)N($R^9$)$_2$, —C(O)$R^9$, C(O)CF$_3$, —(C=NH)$R^9$, N($R^9$)$_2$, $OR^9$, or $SR^9$, wherein at least one $R^2$ and $R^4$ is not hydrogen;

$R^3$ is —$CO_2R^9$, —C(O)N($R^9$)$_2$, —$NR^9$—(C=$NR^9$)N($R^9$)$_2$, —$NR^9$—(C=O)OR$^9$, —O—(C=O)N($R^9$)$_2$, —C(O)$R^9$, C(O)CF$_3$, —(C=NH)$R^9$, N($R^9$)$_2$, $OR^9$, or $SR^9$;

each $R^6$ is independently hydrogen, halo, cyano, ($C_1$-$C_3$) alkyl, ($C_2$-$C_3$) alkenyl, or ($C_2$-$C_3$) alkynyl;

$R^7$ and $R^8$ are independently hydrogen, ($C_1$-$C_6$) alkyl, ($C_2$-$C_6$) alkenyl, ($C_2$-$C_6$) alkynyl, aryl, heteroaryl, cyano, nitro, halo, or trihalomethyl;

each $R^9$ is independently hydrogen, alkyl, or aryl; and

Z is a fluorescent moiety and/or a UV active moiety, wherein Z and Z' are different.

2. The compound of claim 1; wherein $R^1$ and $R^5$ are independently hydrogen or methyl;

R² and R⁴ are independently hydrogen, —CHO, or (CO)($C_1$-$C_6$) alkyl, wherein at least one R² and R⁴ is not hydrogen;

R³ is NH(R⁹) or OH,
wherein R⁹ is hydrogen, ($C_1$-$C_6$) alkyl, or aryl;

R⁶ is hydrogen or methyl;

R⁷ and R⁸ are hydrogen; and

Z is an aryl or heteroaryl group,
wherein the aryl or heteroaryl group may be substituted or unsubstituted.

3. The compound of claim 1; wherein Z is anthracene, a quinoline N-oxide, an isoquinoline N-oxide, or a pyridyl-N-oxide.

4. The compound of claim 1; wherein Z is isoquinoline N-oxide or 4'-pyridyl-N-oxide.

5. The chemosensor of claim 1; wherein the chemosensor is a compound of formula (II):

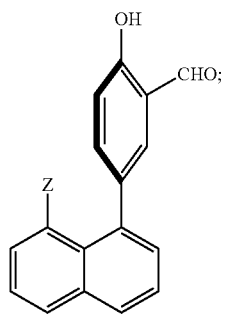

II wherein Z is a fluorescent moiety and/or a UV active moiety.

6. The chemosensor of claim 1; wherein the chemosensor of formula (I) is a compound of formula 3:

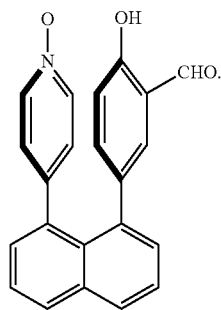

3

7. The chemosensor of claim 1; wherein Z is achiral.

8. The chemosensor of claim 1; wherein the chemosensor compound undergoes racemization and/or diastereomerization in less than about one hour.

9. The chemosensor of claim 5; wherein Z is achiral.

10. The chemosensor of claim 5; wherein the chemosensor compound undergoes racemization and/or diastereomerization in less than about one hour.

11. A method of providing stereoselective recognition of a stereoisomer of a chiral compound;
wherein the method comprises combining a compound of formula (I) from claim 1 with a sample comprising the chiral substrate compound as a mixture of stereoisomers, and
wherein the compound of formula (I) preferentially binds the stereoisomer to form an adduct.

12. The method of claim 11; wherein the method further comprises a step for determining the enantiomeric excess (ee) and diastereomeric excess (de) of the major stereoisomer of the chiral compound by fluorescence spectroscopy, circular dichroism (CD) spectroscopy, and/or ultraviolet (UV) spectroscopy.

13. The method of claim 11; wherein the method further comprises a step for determining the total concentration of the stereoisomer by fluorescence spectroscopy or UV spectroscopy.

14. The method of claim 11; wherein the method further comprises a step for determining the absolute stereochemistry of the stereoisomer of the chiral compound by CD spectroscopy, fluorescence spectroscopy, and/or UV spectroscopy.

15. The method of claim 11; wherein the method further comprises:
(i) isolating the adduct;
(ii) cleaving the adduct;
(iii) separating the compound of formula (I) and the stereoisomer of the chiral compound; and
(iv) isolating the stereoisomer of the chiral compound.

16. The method of claim 11; wherein the compound of formula (I)/chiral compound adduct is diastereomeric with a diastereomeric excess (de) of at least 50% de.

17. The method of claim 15; wherein the isolated stereoisomer of the chiral compound has an enantiomeric excess of at least 50% ee.

18. The method of claim 11; wherein the method further comprises determining two or more of the following properties of the chiral compound:
enantiomeric excess (ee) and/or diastereomeric excess (de) of the major stereoisomer;
the total concentration of the major and/or minor stereoisomer; and/or
the absolute stereochemistry of the major and/or minor stereoisomer.

19. The method of claim 11; wherein the chiral compound has an amine, an amide, a carboxylic acid, an amino alcohol, an amino acid, a thiol, an aldehyde, a ketone or an alcohol function.

20. The method of claim 11; wherein the chiral substrate compound is an amino alcohol.

* * * * *